United States Patent
Jang et al.

(10) Patent No.: US 10,680,182 B2
(45) Date of Patent: Jun. 9, 2020

(54) FLUORANTHENE COMPOUND, AND ORGANIC ELECTRONIC DEVICE COMPRISING SAME

(71) Applicant: LG CHEM, LTD., Seoul (KR)

(72) Inventors: Boonjae Jang, Daejeon (KR); Dong Hoon Lee, Daejeon (KR); Kongkyeom Kim, Daejeon (KR); Minseung Chun, Daejeon (KR); Dong Sik Kim, Daejeon (KR); Kidong Koo, Daejeon (KR); Minyoung Kang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 541 days.

(21) Appl. No.: 14/429,258

(22) PCT Filed: Nov. 19, 2013

(86) PCT No.: PCT/KR2013/010491
§ 371 (c)(1),
(2) Date: Mar. 18, 2015

(87) PCT Pub. No.: WO2014/081168
PCT Pub. Date: May 30, 2014

(65) Prior Publication Data
US 2015/0236273 A1    Aug. 20, 2015

(30) Foreign Application Priority Data

Nov. 21, 2012 (KR) .................. 10-2012-0132190

(51) Int. Cl.
*H01L 51/00* (2006.01)
*C09K 11/06* (2006.01)
(Continued)

(52) U.S. Cl.
CPC ........ *H01L 51/0072* (2013.01); *C07D 209/80* (2013.01); *C07D 209/86* (2013.01);
(Continued)

(58) Field of Classification Search
CPC ............. H01L 51/0054; H01L 51/0067; H01L 51/0074; H01L 51/0073; H01L 51/0058;
(Continued)

(56) References Cited

U.S. PATENT DOCUMENTS

2006/0172147 A1* 8/2006 Matsuura ............ H01L 51/5036
428/690
2007/0243411 A1* 10/2007 Takashima ............. C09K 11/06
428/690
(Continued)

FOREIGN PATENT DOCUMENTS

CN    103319532 A    9/2013
CN    103468243 A    12/2013
(Continued)

OTHER PUBLICATIONS

Kim, et al.: "Substituent Effect of Fluoranthene Derivatives in Electroluminescence", Molecular Crystals and Liquid Crystals, Taylor & Francis Group LLC, vol. 498, 2009, pp. 140-150.
(Continued)

*Primary Examiner* — Alexander C Kollias
(74) *Attorney, Agent, or Firm* — Dentons US LLP

(57) ABSTRACT

The present specification provides a novel fluoranthene compound significantly improving the life span, efficiency, electrical and chemical stability and thermal stability of an organic electronic device, and an organic electronic device that contains the compound in an organic compound layer.

16 Claims, 1 Drawing Sheet

(51) Int. Cl.
| | |
|---|---|
| C07D 221/10 | (2006.01) |
| C07D 333/76 | (2006.01) |
| C07D 239/26 | (2006.01) |
| C07D 251/24 | (2006.01) |
| C07D 471/04 | (2006.01) |
| C07D 487/04 | (2006.01) |
| C07D 307/91 | (2006.01) |
| C07D 307/79 | (2006.01) |
| C07D 333/54 | (2006.01) |
| C07D 471/14 | (2006.01) |
| C07D 209/86 | (2006.01) |
| H05B 33/14 | (2006.01) |
| C07D 209/80 | (2006.01) |
| C07D 221/18 | (2006.01) |
| C07D 239/74 | (2006.01) |
| C07D 401/04 | (2006.01) |
| C07F 9/535 | (2006.01) |
| H01L 51/50 | (2006.01) |
| H01L 51/05 | (2006.01) |
| H01L 51/44 | (2006.01) |
| H01L 51/52 | (2006.01) |

(52) U.S. Cl.
CPC ......... *C07D 221/10* (2013.01); *C07D 221/18* (2013.01); *C07D 239/26* (2013.01); *C07D 239/74* (2013.01); *C07D 251/24* (2013.01); *C07D 307/79* (2013.01); *C07D 307/91* (2013.01); *C07D 333/54* (2013.01); *C07D 333/76* (2013.01); *C07D 401/04* (2013.01); *C07D 471/04* (2013.01); *C07D 471/14* (2013.01); *C07D 487/04* (2013.01); *C07F 9/535* (2013.01); *C09K 11/06* (2013.01); *H01L 51/0054* (2013.01); *H01L 51/0058* (2013.01); *H01L 51/0067* (2013.01); *H01L 51/0073* (2013.01); *H01L 51/0074* (2013.01); *H05B 33/14* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *C09K 2211/1096* (2013.01); *H01L 51/006* (2013.01); *H01L 51/0558* (2013.01); *H01L 51/441* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 51/5206* (2013.01); *H01L 51/5221* (2013.01); *H01L 2251/301* (2013.01); *H01L 2251/308* (2013.01); *Y02E 10/549* (2013.01)

(58) Field of Classification Search
CPC ............. H01L 51/0072; H01L 51/0558; H01L 51/441; H01L 51/5096; H01L 51/5088; H01L 51/5056; H01L 51/5092; H01L 51/5072; H01L 51/5012; H01L 51/5221; H01L 51/5206; H01L 2251/301; C07D 471/04; C07D 239/26; C07D 251/24; C07D 221/18; C07D 239/74; C07D 401/04; C07D 487/04; C07D 209/80; C07D 333/76; C07D 307/91; C07D 221/10; C07F 9/535; C09K 11/06; C09K 2211/1096; C09K 2211/1088; C09K 2211/1092; C09K 2211/1059; C09K 2211/1044; C09K 2211/1029
See application file for complete search history.

(56) References Cited

U.S. PATENT DOCUMENTS

| | | | |
|---|---|---|---|
| 2011/0248257 A1 | 10/2011 | Kim et al. | |
| 2012/0097924 A1 | 4/2012 | Kim et al. | |
| 2014/0114069 A1* | 4/2014 | Kim | C09K 11/06 544/229 |
| 2015/0108449 A1* | 4/2015 | Huang | C07F 9/5325 548/310.7 |

FOREIGN PATENT DOCUMENTS

| | | | | |
|---|---|---|---|---|
| JP | 2003-105332 A | 4/2003 | | |
| JP | 2012-092099 A | 5/2012 | | |
| JP | 2012-513987 A | 6/2012 | | |
| JP | 2014-531419 A | 11/2014 | | |
| KR | 1020110137897 A | 12/2011 | | |
| KR | 1020120029258 A | 3/2012 | | |
| KR | 10-2013-0025087 A | 3/2013 | | |
| TW | 201404862 A | 2/2014 | | |
| WO | WO-2012030145 A1 * | 3/2012 | ........... | C09D 401/04 |
| WO | 2013/182046 A1 | 12/2013 | | |

OTHER PUBLICATIONS

Tong, Qing-Xiao et al., High-efficiency nondoped green organic light-emitting devices, Chemical Physics Letters, 2008, pp. 79-82, vol. 455.
Chinese Office Action with English translation dated Nov. 18, 2015 in Chinese Patent Application No. 2013800527278 (14 pages).
Boonjae Jang, U.S. Appl. No. 14/429,258, filed Mar. 18, 2015, Fluoranthene Compound, and Organic Electronic Device Comprising Same.

* cited by examiner

[FIG. 1]
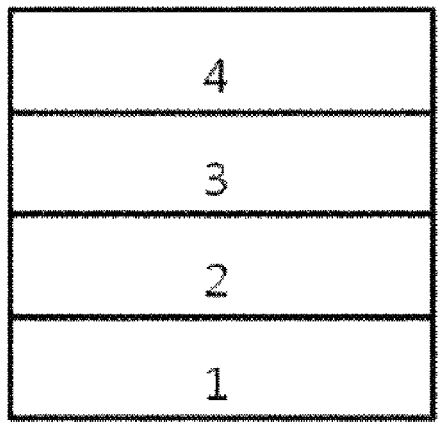
[FIG. 2]
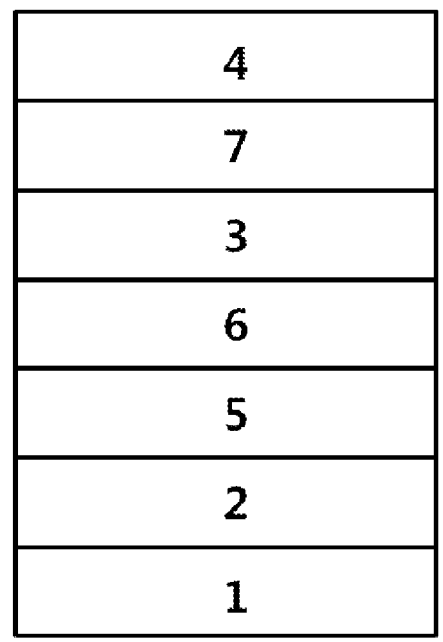

FLUORANTHENE COMPOUND, AND ORGANIC ELECTRONIC DEVICE COMPRISING SAME

This application is a National Stage Application of International Application No. PCT/KR2013/010491, filed Nov. 19, 2013, and claims the benefit of Korean Patent Application No. 10-2012-0132190 filed on Nov. 21, 2012, all of which are hereby incorporated by reference in their entirety for all purposes as if fully set forth herein.

FIELD OF THE INVENTION

The present specification relates to a fluoranthene compound and an organic electronic device including the same.

BACKGROUND OF THE INVENTION

An organic electronic device means a device that needs charge exchanges between an electrode and an organic material using holes and/or electrons. An organic electronic device can be categorized into two main groups depending on the operation principle. First is an electric device in which excitons form in an organic material layer by the photons brought into the device from an external source, these excitons are separated into electrons and holes, and these electrons and holes are used as a current source (voltage source) by being transferred to different electrodes. Second is an electronic device in which holes and/or electrons are injected to an organic material semiconductor that forms an interface with an electrode by applying voltage or current to two or more electrodes, and the device is operated by the injected electrons and holes.

Examples of an organic electronic device include an organic light emitting device, an organic solar cell, an organic photo conductor (OPC), an organic transistor, and the like, and these all need a hole injection or transfer material, an electron injection or transfer material, or a light emitting material for the driving of the device. Hereinafter, an organic light emitting device will be described in detail, however, in the organic electronic devices, a hole injection or transfer material, an electron injection or transfer material, or a light emitting material is used under similar principles.

An organic light emission phenomenon generally refers to a phenomenon that converts electric energy to light energy using an organic material. An organic light emitting device using an organic light emission phenomenon typically has a structure that includes an anode, a cathode, and an organic material layer therebetween. Herein, the organic material layer is usually formed as a multilayer structure formed with different materials in order to improve the efficiency and the stability of an organic light emitting device, and for example, may be formed with a hole injection layer, a hole transfer layer, a light emitting layer, an electron transfer layer, an electron injection layer, and the like. In the structure of such an organic light emitting device, holes from an anode and electrons from a cathode flow into an organic material layer when voltage is applied between the two electrodes, excitons form when the electrons and the holes injected are combined, and light emits when these excitons fall back to the ground state. Such an organic light emitting device has been known to have characteristics such as spontaneous light emission, high brightness, high efficiency, low driving voltage, wide viewing angle, high contrast, and quick response.

In an organic light emitting device, the material used as an organic material layer can be divided into a light emitting material and a charge transfer material, for example, a hole injection material, a hole transfer material, an electron transfer material, an electron injection material and the like, depending on the function. In addition, the light emitting material can be divided into, depending on the light emitting color, a blue, a green and a red light emitting material, and a yellow and an orange light emitting material to obtain better natural color. Meanwhile, when only one material is used as the light emitting material, problems occur such as the maximum light emitting wavelength moving to a long wavelength due to the interaction between molecules, color purity being reduced, or the efficiency of the device being reduced due to a light emission diminution effect. Therefore, a host/dopant-based material may be used as the light emitting material in order to increase color purity and increase light emission efficiency through the energy transfer.

In order for an organic light emitting device to exhibit excellent characteristics described above, materials that form an organic material layer, for example, a hole injection material, a hole transfer material, a light emitting material, an electron transfer material, an electron injection material, and the like, need to be supported by stable and efficient materials first, however, the development of stable and efficient materials of an organic material layer for an organic light emitting device has not been sufficient so far. Therefore, there have been continuous demands for the development of new materials, and the needs for the development of such materials also apply to other organic electronic devices described above.

SUMMARY OF THE INVENTION

In view of the above, an objective of the present application is to provide a fluoranthene compound derivative having a chemical structure that can perform various roles required in an organic electronic device depending on substituents, and provide an organic electronic device including the fluoranthene compound derivative.

The present specification provides a fluoranthene compound represented by the following Chemical Formula 1.

[Chemical Formula 1]

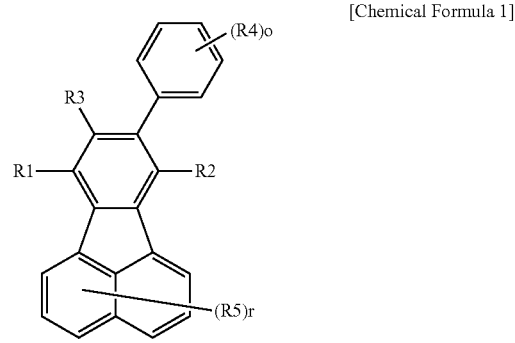

In Chemical Formula 1,
R1 to R3 are groups represented by -(L)p-(Y)q,
p is an integer of 0 to 10 and q is an integer of 1 to 10,
o is an integer of 1 to 5,
r is an integer of 0 to 6,
L is a substituted or unsubstituted arylene group; a substituted or unsubstituted alkenylene group; a substituted or unsubstituted fluorenylene group; or a substituted or unsubstituted heteroarylene group having O, N, S or P as a heteroatom, Y is hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted phosphine oxide group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heteroring group including one or more of N, O, S and P atoms, when p≥2 or q≥2, Ls or Ys are the same as or different from each other, R1 and R3 may be bonded to each other to form an aliphatic ring, an aromatic ring, an aliphatic heteroring or an aromatic heteroring, or form a spiro bond, when o≥2, R4s are the same as or different from each other, R4 is an aryl group substituted with a substituent selected from the group consisting of a substituted or unsubstituted heteroring group including a 5-membered ring or a 6-membered ring that includes one or more of O, S and P atoms, a substituted or unsubstituted monocyclic or multicyclic heteroring group including a 6-membered ring that includes one or more Ns, a substituted or unsubstituted benzocarbazole group, and a substituted or unsubstituted phosphine oxide group; a substituted or unsubstituted phosphine oxide group; a substituted or unsubstituted heteroring group including a 5-membered ring or a 6-membered ring that includes one or more of O, S and P atoms; a substituted or unsubstituted benzocarbazole group; or a substituted or unsubstituted monocyclic or multicyclic heteroring group including a 6-membered ring that includes one or more Ns, or adjacent groups among a plurality of R4s may form an aliphatic ring, an aromatic ring, an aliphatic heteroring or an aromatic heteroring, or form a spiro bond, when r≥2, R5s are the same as or different from each other, R5 is hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted phosphine oxide group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heteroring group including one or more of N, O, S and P atoms, or adjacent groups among a plurality of R5s are bonded to each other to form an aliphatic ring, an aromatic ring, an aliphatic heteroring or an aromatic heteroring, or form a spiro bond.

In addition, the present specification provides an organic electronic device that includes a first electrode, a second electrode, and one or more layers of organic material layers disposed between the first electrode and the second electrode, wherein one or more layers of the organic material layers include the fluoranthene compound of Chemical Formula 1.

Advantageous Effects

A fluoranthene derivative according to the present specification can be used as an organic material layer of an organic electronic device including an organic light emitting device, and the organic electronic device including the organic light emitting device using the fluoranthene derivative can have improved efficiency, low driving voltage and/or improved life span characteristics.

BRIEF DESCRIPTION OF THE DRAWINGS

FIG. 1 shows an example of an organic electronic device formed with a substrate (1), an anode (2), a light emitting layer (3) and a cathode (4) by a diagram.

FIG. 2 shows an example of an organic electronic device formed with a substrate (1), an anode (2), a hole injection layer (5), a hole transfer layer (6), a light emitting layer (3), an electron transfer layer (7) and a cathode (4) by a diagram.

DETAILED DESCRIPTION OF THE EMBODIMENTS

The present specification provides a fluoranthene compound represented by Chemical Formula 1.

In addition, the compound represented by Chemical Formula 1 of the present specification may be represented by the following Chemical Formula 2.

[Chemical Formula 2]

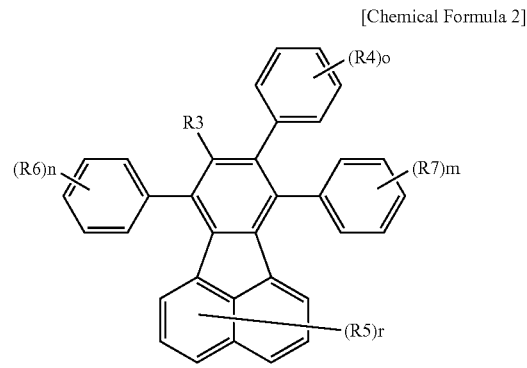

In Chemical Formula 2, o, r, and R3 to R5 are the same as those defined in Chemical Formula 1, each of n and m is an integer of 0 to 5, when n≥2, R6s are the same as or different from each other, when m≥2, R7s are the same as or different from each other, R6 and R7 are the same as or different from each other, each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted phosphine oxide group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heteroring group including one or more of N, O, S and P atoms, or adjacent groups may be bonded to each other to form an aliphatic ring, an aromatic ring, an aliphatic heteroring or an aromatic heteroring, or form a spiro bond.

Examples of the substituents are described below, but are not limited thereto.

In addition, in the present specification, the term "substituted or unsubstituted" means being substituted with one or more substituents selected from the group consisting of deuterium; a halogen group; an alkyl group; an alkenyl group; an alkoxy group; a cycloalkyl group; a silyl group; an arylalkenyl group; an aryl group; an aryloxy group; an alkylthioxy group; an alkylsulfoxy group; an arylsulfoxy group; a boron group; an alkylamine group; an aralkylamine group; an arylamine group; a heteroaryl group; a carbazole group; an arylamine group; an aryl group; a fluorenyl group; a nitrile group; a nitro group; a hydroxy group; a cyano group, and a heteroring group including one or more of N, O, S and P atoms, or having no substituents.

In the present specification, an alkyl group may be linear or branched, and although not particularly limited, the number of carbon atoms is preferably 1 to 50. Specific examples thereof include a methyl group, an ethyl group, a propyl group, an isopropyl group, a butyl group, a t-butyl group, a pentyl group, a hexyl group, a heptyl group and the like, but are not limited thereto.

In the present specification, the alkenyl group may be linear or branched, and although not particularly limited, the number of carbon atoms is preferably 2 to 50. Specific examples thereof preferably include an alkenyl group in which an aryl group such as a stilbenyl group or a styrenyl group is substituted, but are not limited thereto.

In the present specification, the alkoxy group may be linear or branched, and although not particularly limited, the number of carbon atoms is preferably 1 to 50.

The length of the alkyl group, the alkenyl group and the alkoxy group included in the compound does not have an influence on the conjugation length of the compound, and only concomitantly has an influence on the application method of the compound to an organic electronic device, for example, on the application of a vacuum deposition method or a solution coating method, therefore, the number of carbon atoms is not particularly limited.

In the present specification, the cycloalkyl group is not particularly limited, however, the number of carbon atoms is preferably 3 to 60, and particularly, a cyclopentyl group or a cyclohexyl group is preferable.

In the present specification, the aryl group may be monocyclic or multicyclic, and although not particularly limited, the number of carbon atoms is preferably 6 to 60. Specific examples of the aryl group include a monocyclic aromatic group such as a phenyl group, a biphenyl group, a triphenyl group, a terphenyl group or a stilbenyl group, and a multicyclic aromatic group such as a naphthyl group, a binaphthyl group, an anthracenyl group, a phenanthrenyl group, a pyrenyl group, a perylenyl group, a tetracenyl group, a crycenyl group, a fluorenyl group, an acenaphthacenyl group, a triphenylene group or a fluoranthene group, but are not limited thereto.

In the present specification, the heteroring group is a heteroring group that includes O, N, S and P as a heteroatom, and although not particularly limited, the number of carbon atoms is preferably 2 to 60. Examples of the heteroring group include a thiophene group, a furan group, a pyrrole group, an imidazole group, a thiazole group, an oxazole group, an oxadiazole group, a triazole group, a pyridyl group, a bipyridyl group, a triazine group, an acridyl group, a pyridazine group, a qinolinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a dibenzofuranyl group or the like, but are not limited thereto.

In the present specification, examples of the monocyclic or multicyclic heteroring group including a 6-membered ring that includes one or more Ns include a pyridine group, a pyrimidine group, a pyridazine group, a pyrazine group, a triazine group, a tetrazine group, a pentazine group, a quinoline group, a cynoline group, a quinazoline group, a quinoxaline group, a pyridopyrazine group, a pyrazinopyrazine group, a pyrazinoquinoxaline group, an acridine group, a phenanthroline group or the like, but are not limited thereto.

In the present specification, the monocyclic or multicyclic heteroring group including a 6-membered ring that includes one or more Ns is a heteroring group including at least one or more 6-membered rings that include one or more Ns, and also includes a heteroring group in which a 5-membered ring is fused to a 6-membered ring that includes one or more Ns. In other words, other 5-membered rings or 6-membered rings different from the specific examples described above may be additionally fused, and the fused 5-membered ring or 6-membered ring may be an aromatic ring, an aliphatic ring, an aliphatic heteroring and/or an aromatic heteroring.

In the present specification, examples of the halogen group include fluorine, chlorine, bromine or iodine.

In the present specification, the fluorenyl group has a structure in which two cyclic organic compounds are linked through one atom, and examples thereof include

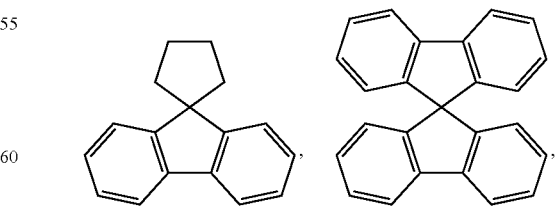

or the like.

In the present specification, the fluorenyl group includes the structure of an open fluorenyl group, and herein, the open fluorenyl group has a structure in which the linkage of one ring compound is broken in the structure of two ring compounds linked through one atom, and examples thereof include

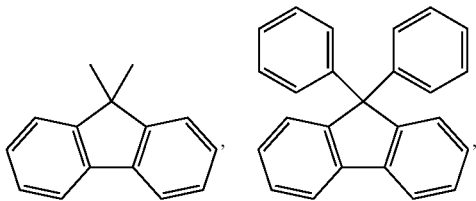

or the like.

In the present specification, the number of carbon atoms of the amine group is not particularly limited, but is preferably 1 to 50. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group or the like, but are not limited thereto.

In the present specification, the number of carbon atoms of the arylamine group is not particularly limited, but is preferably 6 to 50. Examples of the arylamine group include a substituted or unsubstituted monocyclic diarylamine group, a substituted or unsubstituted multicyclic diarylamine group or a substituted or unsubstituted monocyclic and monocyclic diarylamine group.

In the present specification, the number of carbon atoms of the aryloxy group, the arylthioxy group, the arylsulfoxy group and the aralkylamine group is not particularly limited, but is preferably 6 to 50. The aryl group in the aryloxy group, the arylthioxy group, the arylsulfoxy group and the aralkylamine group is the same as the examples of the aryl group described above.

In the present specification, the alkyl group in the alkylthioxy group, the alkylsulfoxy group, the alkylamine group and the aralkylamine group is the same as the examples of the alkyl group described above.

In the present specification, the heteroaryl group in a heteroarylamine group may be selected from among the examples of the heteroring group described above.

In the present specification, the arylene group, the alkenylene group, the fluorenylene group, and the heteroarylene group are divalent groups of the aryl group, the alkenyl group, the fluorenyl group, and the heteroaryl group, respectively. Descriptions for the aryl group, the alkenyl group, the fluorenyl group and the heteroaryl group may be applied to the arylene group, the alkenylene group, the fluorenylene group, and the heteroarylene group, except that these are divalent groups.

In the present specification, the substituted arylene group means that a phenyl group, a biphenyl group, a naphthyl group, a fluorenyl group, a pyrenyl group, a phenanthrenyl group, a perylene group, a tetracenyl group, an anthracenyl group, or the like, is substituted with other substituents.

In the present specification, the substituted heteroarylene group means that a pyridyl group, a thiophenyl group, a triazine group, a quinoline group, a phenanthroline group, an imidazole group, a thiazole group, an oxazole group, a carbazole group, and fused heteroring groups thereof such as a benzoquinoline group, a benzimidazole group, a benzoxazole group, a benzothiazole group, a benzocarbazole group, a dibenzothiophenyl group, or the like, is substituted with other substituents.

An adjacent group in the present specification means each neighboring substituent when there are two or more substituents.

In the present specification, forming an aliphatic ring, an aromatic ring, an aliphatic heteroring or an aromatic heteroring with an adjacent group means that each of the adjacent substituents forms a bond to form a 5-membered to 7-membered multicyclic or monocyclic ring.

In the present specification, a spiro bond means a structure in which two cyclic organic compounds are linked to one atom, and may include a structure in which the linkage of one ring compound is broken in the structure of two cyclic organic compounds linked through one atom.

The present specification provides a novel fluoranthene compound represented by Chemical Formula 1. The compound may be used as an organic material layer in an organic electronic device due to its structural specificity.

In one embodiment of the present specification, R1 to R3 are represented by -(L)p-(Y)q.

In one embodiment of the present specification, p is an integer of 0 to 10.

In one embodiment of the present specification, p is 1.

In one embodiment of the present specification, p is 0.

In one embodiment of the present specification, q is an integer of 1 to 10.

In one embodiment of the present specification, q is 1.

In one embodiment of the present specification, L is a substituted or unsubstituted arylene group, a substituted or unsubstituted fluorenylene group, or a substituted or unsubstituted heteroarylene group.

In one embodiment of the present specification, L is a substituted or unsubstituted arylene group.

In one embodiment of the present specification, L is a substituted or unsubstituted phenylene group.

In one embodiment of the present specification, Y is hydrogen.

In one embodiment of the present specification, R4 is a substituted or unsubstituted benzoquinoline group; a substituted or unsubstituted phenanthroline group; a substituted or unsubstituted pyrimidine group; a substituted or unsubstituted triazine group; a substituted or unsubstituted benzophenanthridine group; a substituted or unsubstituted quinoline group; a substituted or unsubstituted carbazole group; a substituted or unsubstituted benzocarbazole group; a substituted or unsubstituted dibenzothiophene group; a substituted or unsubstituted dibenzofuran group; a substituted or unsubstituted phosphine oxide group; a substituted or unsubstituted benzothiophene group; or a substituted or unsubstituted benzofuran group; or a substituted or unsubstituted quinazoline group.

In one embodiment of the present specification, R4 forms an aliphatic ring by being bonded to an adjacent group.

In one embodiment of the present specification, R4 forms an aromatic ring by being bonded to an adjacent group.

In one embodiment of the present specification, R4 is a phenyl group substituted with at least one of the following substituents; or is at least one of the following substituents, or a plurality of adjacent R4s form a hydrocarbon ring substituted with at least one of the following substituents with each other.

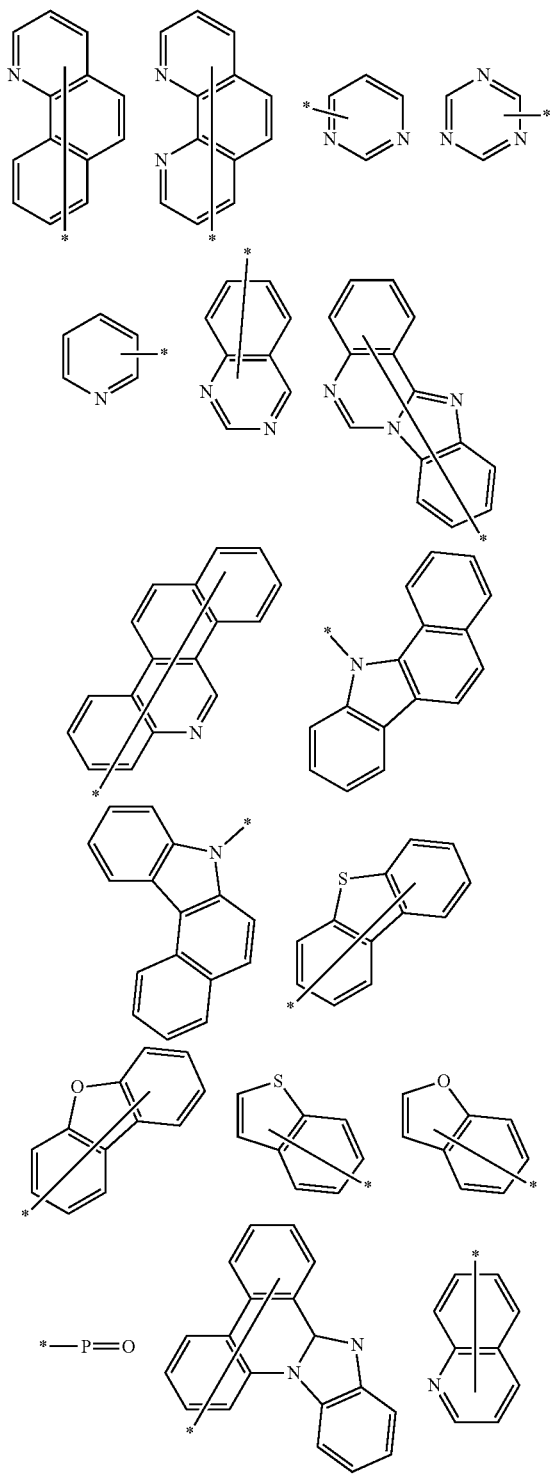

* means being linked to a hydrocarbon ring formed by Chemical Formula 1, a phenyl group or a plurality of adjacent R4s being bonded to each other, The substituents may be unsubstituted or additionally substituted with substituents selected from the group consisting of a substituted or unsubstituted alkyl group; a substituted or unsubstituted aryl group; and a substituted or unsubstituted heteroring group including one or more of N, O, S and P atoms.

In one embodiment of the present specification, the substituents are additionally substituted with hydrogen; a methyl group; an ethyl group; a phenyl group; a naphthyl group; a biphenyl group; or a pyridine group.

In one embodiment of the present specification, the hydrocarbon ring may be an aromatic ring, an aliphatic ring, or a fused ring of an aliphatic ring and an aromatic ring, and may be monocyclic or multicyclic.

In the substituents, "being substituted" means that a hydrogen atom bonded to the carbon atom of a compound is replaced with other atoms or functional groups, and "substituent" includes all of hydrogen, other atoms and functional groups. The substitution position in the present specification is not limited as long as it is a position at which a hydrogen atom is substituted, that is, a position that can be substituted with substituents, and when two or more are substituted, the two or more substituents may be the same as or different from each other.

In one embodiment of the present specification, R4 is a substituted or unsubstituted benzoquinoline group.

In one embodiment of the present specification, R4 is a substituted or unsubstituted phenanthroline group.

In one embodiment of the present specification, R4 is a substituted or unsubstituted pyrimidine group.

In one embodiment of the present specification, R4 is a pyrimidine group substituted with a phenyl group.

In one embodiment of the present specification, R4 is a pyrimidine group substituted with a biphenyl group.

In one embodiment of the present specification, R4 is a substituted or unsubstituted triazine group.

In one embodiment of the present specification, R4 is a triazine group substituted with a phenyl group.

In one embodiment of the present specification, R4 is a triazine group substituted with a naphthyl group.

In one embodiment of the present specification, R4 is a substituted or unsubstituted benzophenanthridine group.

In one embodiment of the present specification, R4 is a substituted or unsubstituted quinoline group.

In one embodiment of the present specification, R4 is a quinoline group substituted with a phenyl group.

In one embodiment of the present specification, R4 is a quinoline group substituted with a pyridine group.

In one embodiment of the present specification, R4 is a substituent having a structure in which a phenanthridine group and a benzimidazole group are bonded.

In one embodiment of the present specification, R4 is a substituent having a structure in which a quinoline group and a benzimidazole group are bonded.

In one embodiment of the present specification, R4 is a substituted or unsubstituted benzocarbazole group. The benzocarbazole group is either

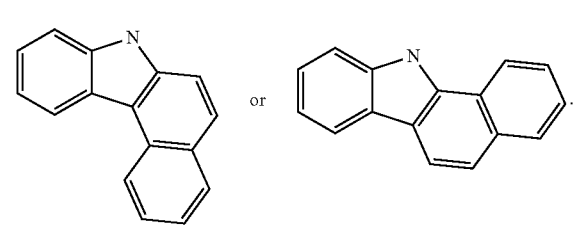 [SMILES: c1ccc2c(c1)ccc1[nH]c3ccccc3c12 ; c1ccc2c(c1)ccc1c3ccccc3[nH]c21]

In one embodiment of the present specification, R4 is a substituted or unsubstituted dibenzothiophene group. The dibenzothiophene group is linked to the fluoranthene core of the present compound at position 6 or position 2 of the following dibenzothiophene group structure.

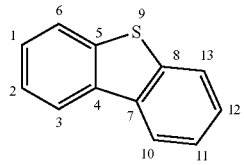

In one embodiment of the present specification, R4 is a substituted or unsubstituted dibenzofuran group. The dibenzofuran group is linked to the fluoranthene core of the present compound at position 6 or position 2 of the following dibenzofuran group structure.

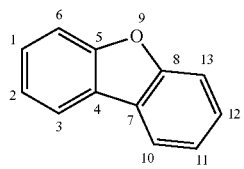

In one embodiment of the present specification, R4 is a substituted or unsubstituted phosphine oxide group.

In one embodiment of the present specification, R4 is a phosphine oxide group substituted with a phenyl group.

In one embodiment of the present specification, R4 is substituted or unsubstituted benzothiophene.

In one embodiment of the present specification, R4 is benzothiophene substituted with a phenyl group.

In one embodiment of the present specification, R4 is substituted or unsubstituted benzofuran.

In one embodiment of the present specification, R4 is benzofuran substituted with a phenyl group.

In one embodiment of the present specification, R4 is a substituted or unsubstituted quinazoline group.

In one embodiment of the present specification, R4 is a quinazoline group substituted with a phenyl group.

In one embodiment of the present specification, R4 is a substituted or unsubstituted phenanthrene group.

In one embodiment of the present specification, R4 is a substituted or unsubstituted a pyridine group.

In one embodiment of the present specification, R4 is a pyridine group substituted with a pyridine group.

Preferable specific examples of the compound according to the present specification include the following compounds, but are not limited thereto.

In one embodiment of the present specification, R4 is any one of the following structural formulae.

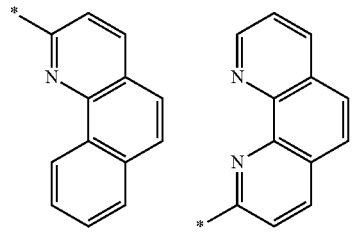

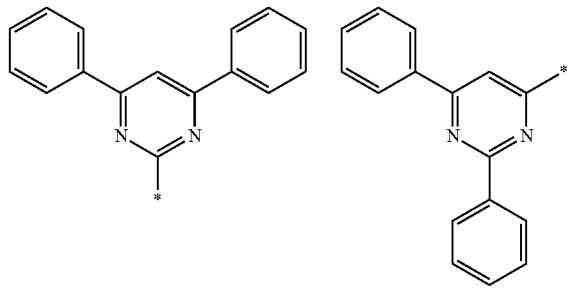

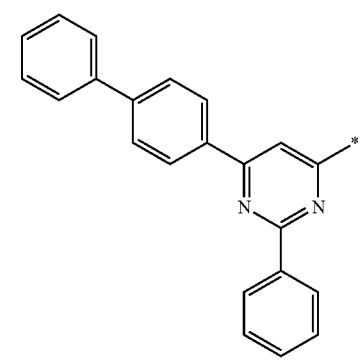

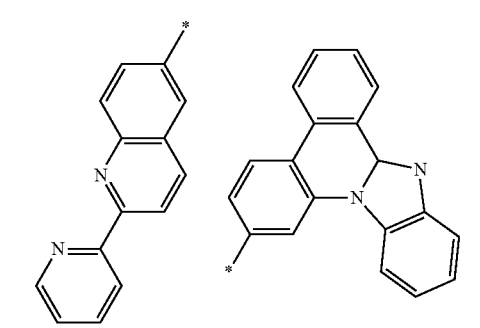

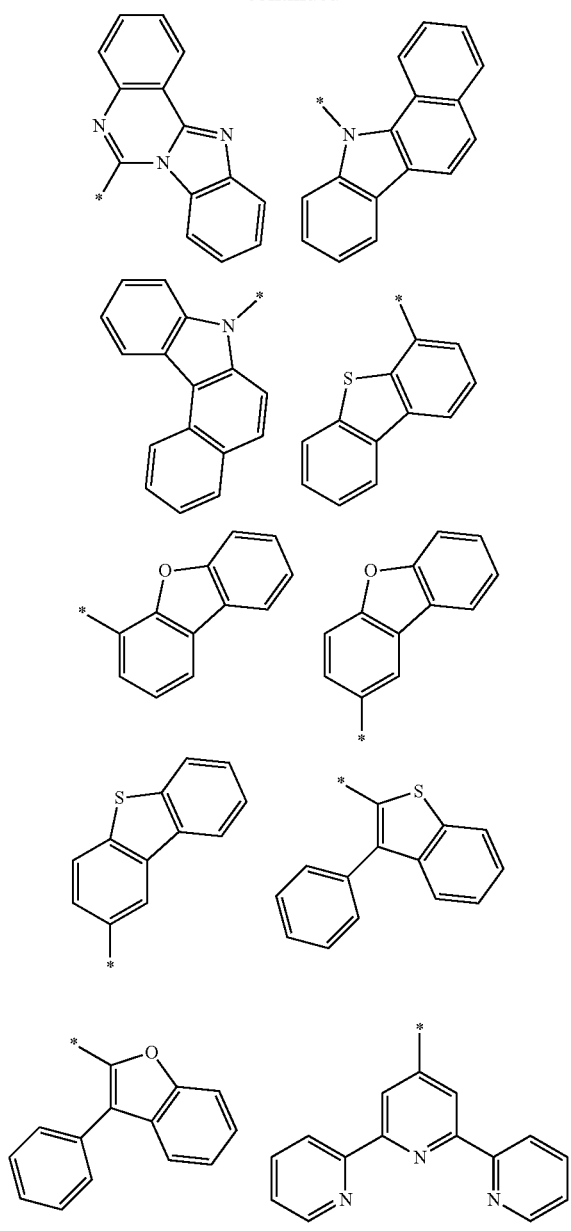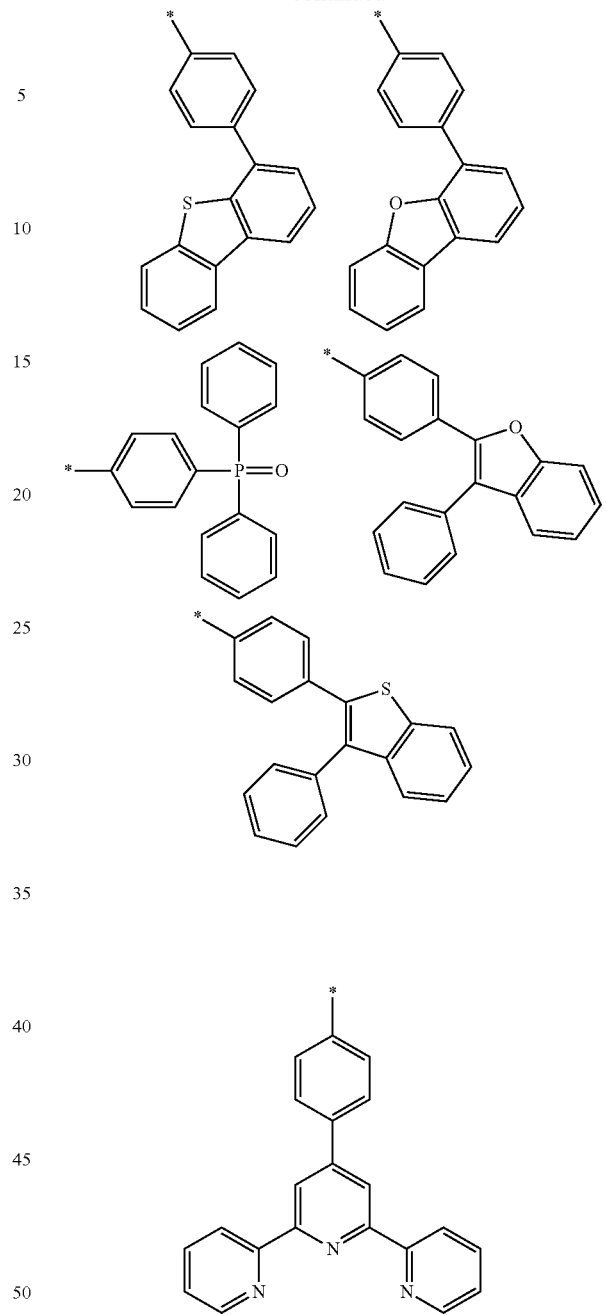
In one embodiment of the present specification, R4 is any one of the following structural formulae.
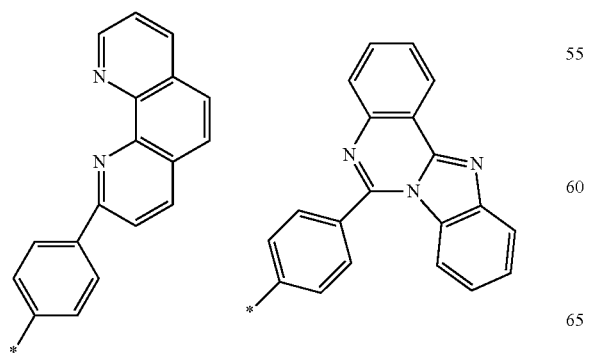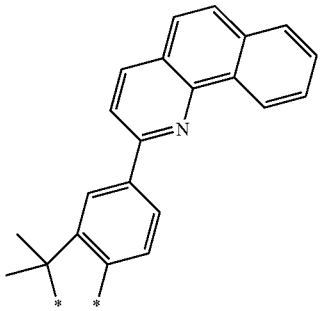

-continued
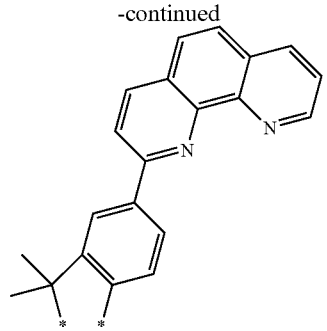
In one embodiment of the present specification, Chemical Formula 1 is represented by any one of the following Compounds 1 to 38.
Compound 1
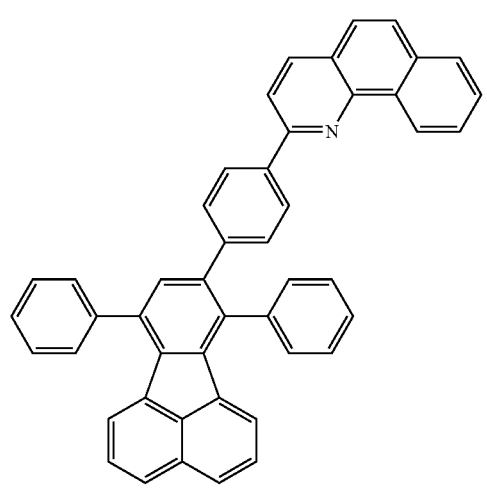
Compound 2
Compound 3
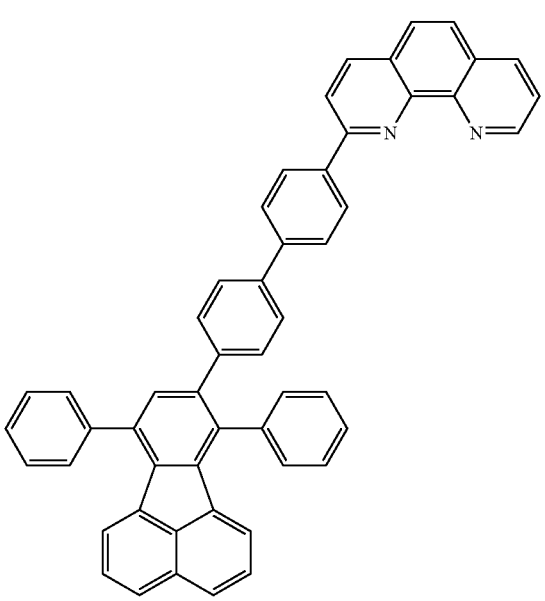
Compound 4
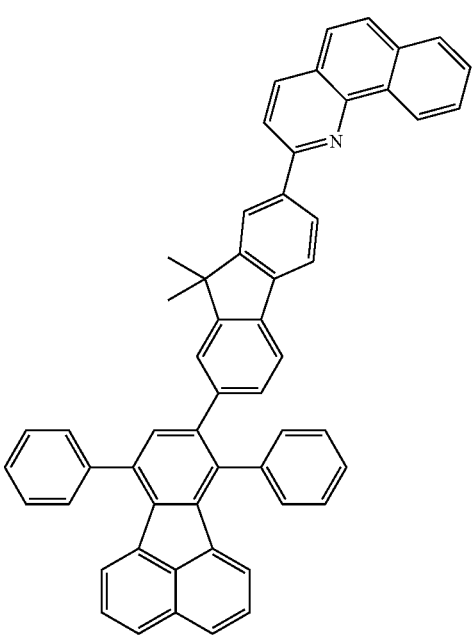

Compound 5
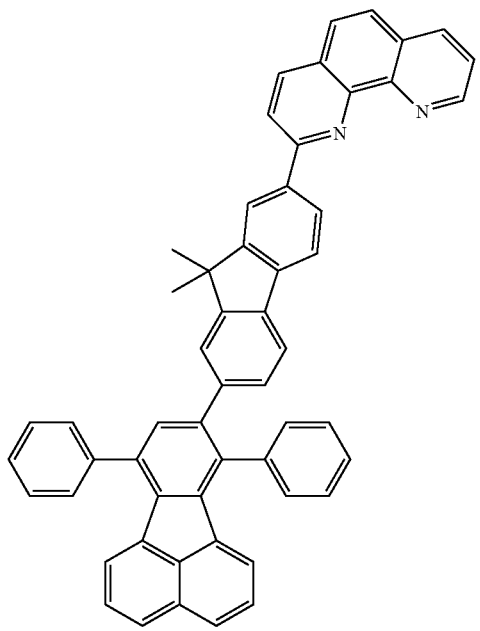
Compound 6
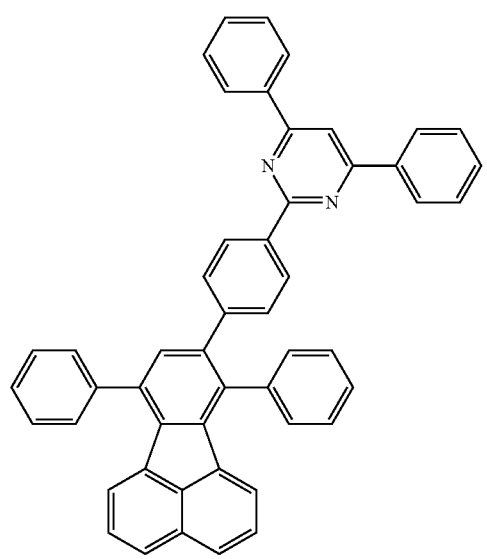
Compound 7
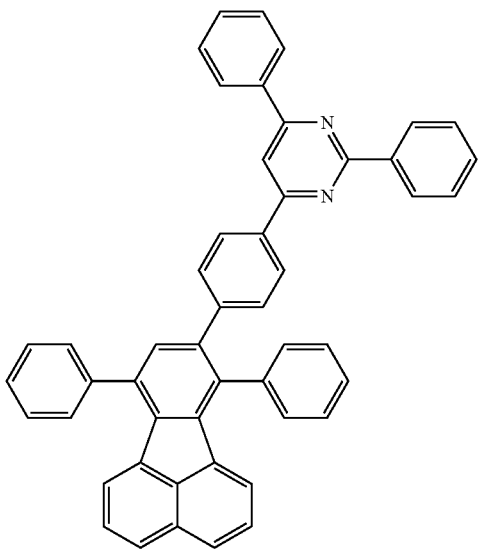
Compound 8
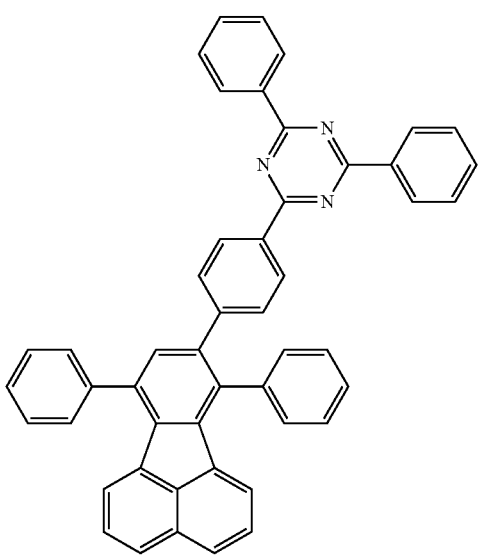

-continued
Compound 9
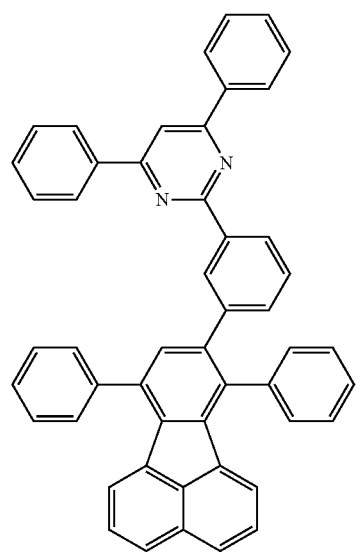
Compound 10
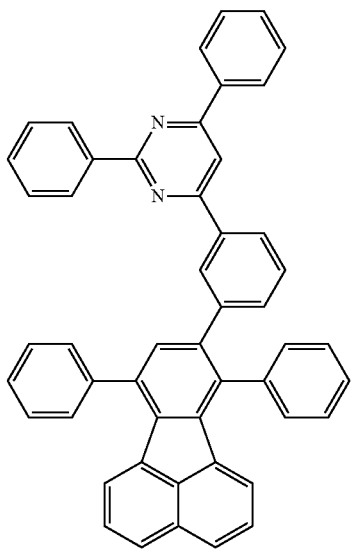
Compound 11
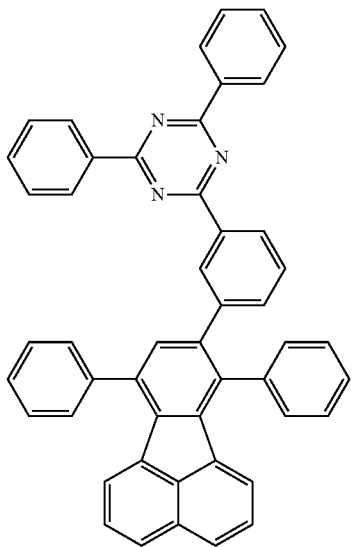
-continued
Compound 12
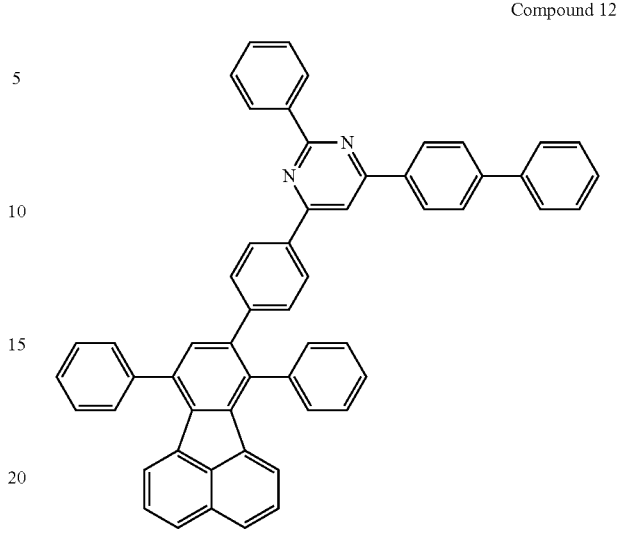
Compound 13
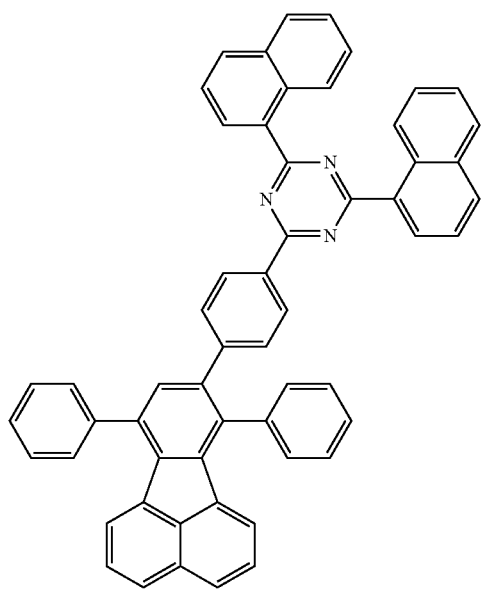

Compound 14
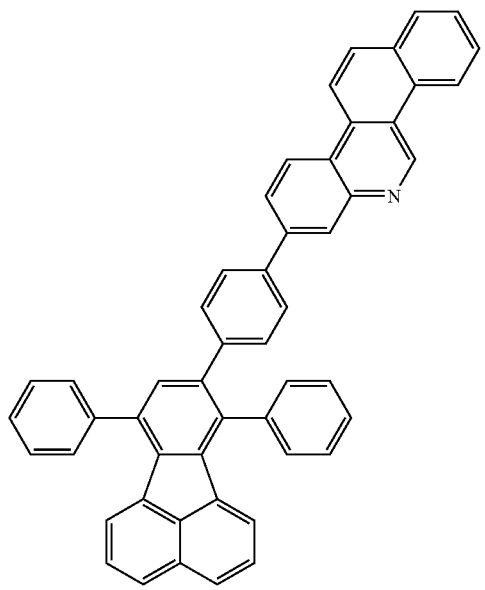
Compound 15
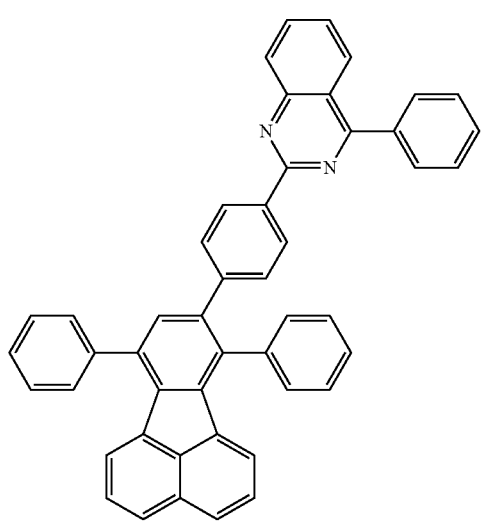
Compound 16
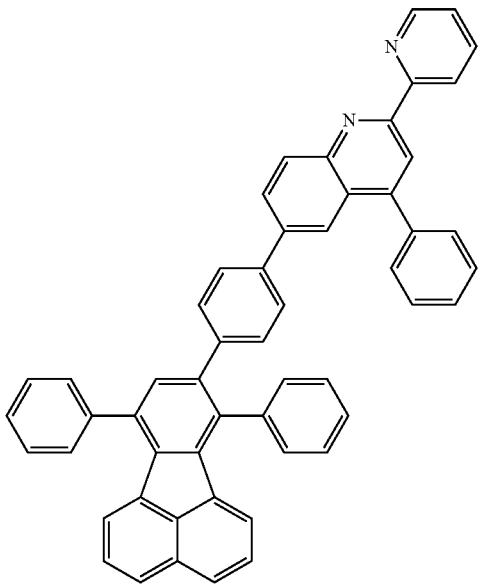
Compound 17

Compound 18
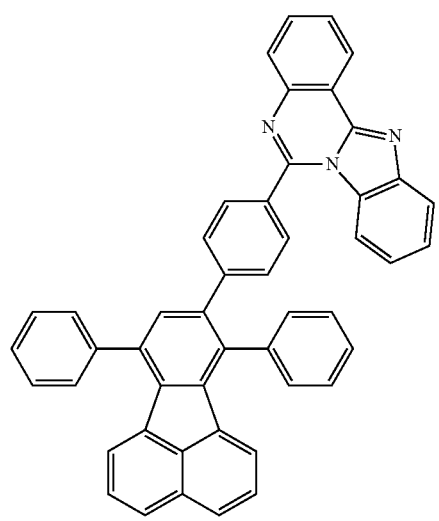
Compound 19
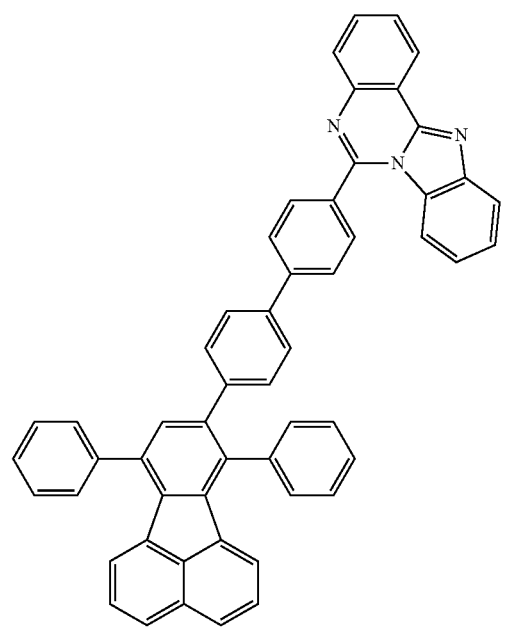
Compound 20
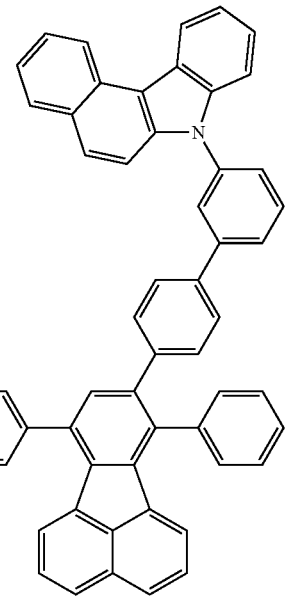
Compound 21
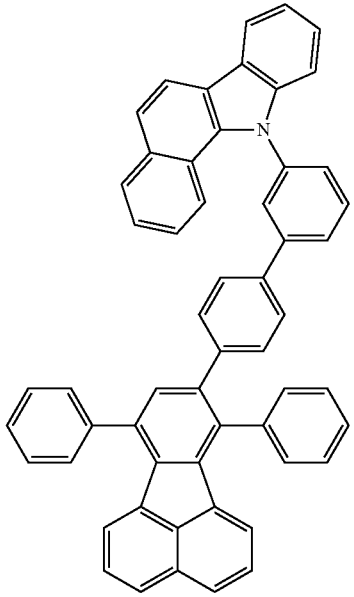

Compound 22
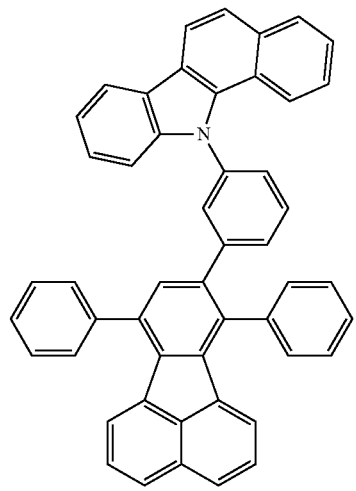
Compound 23
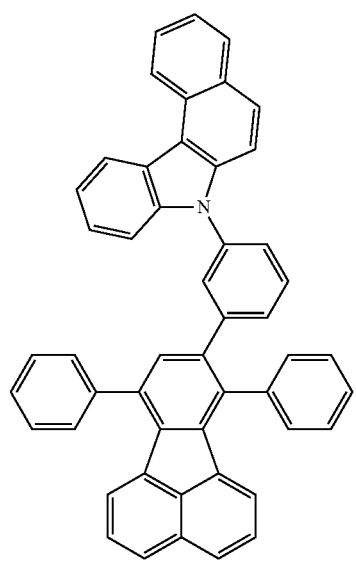
Compound 24
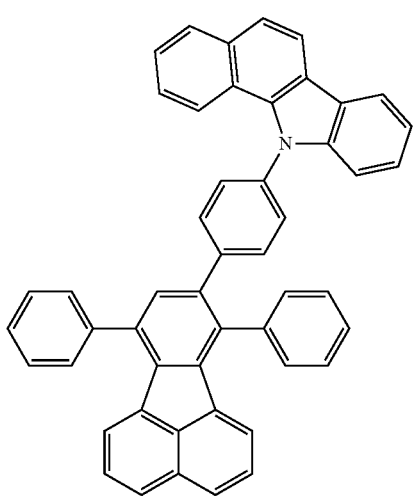
Compound 25
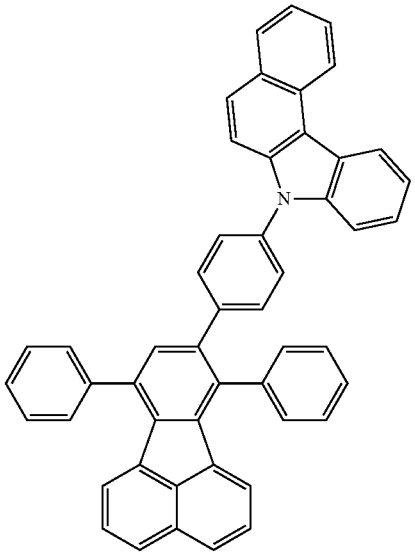
Compound 26
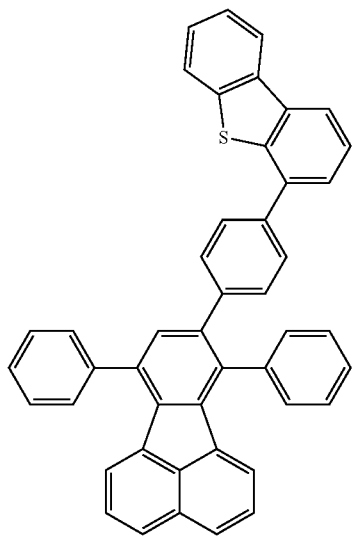
Compound 27
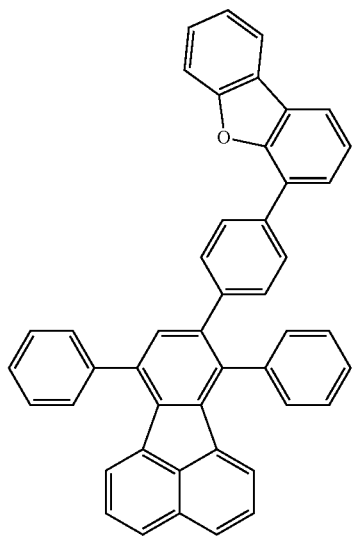

Compound 28
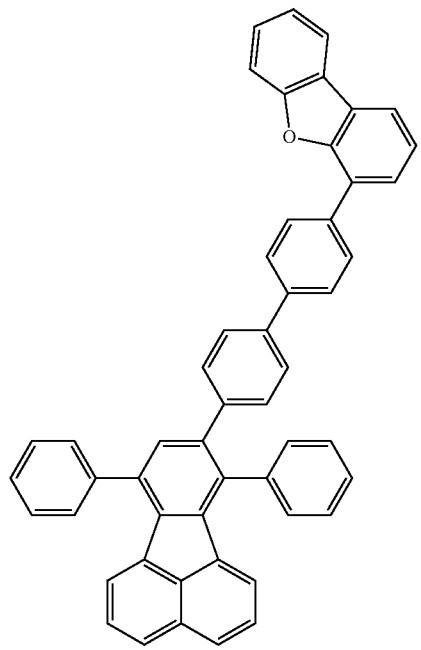
Compound 29
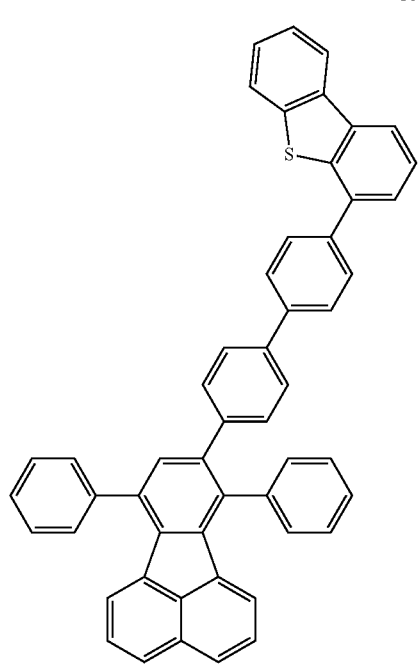
Compound 30
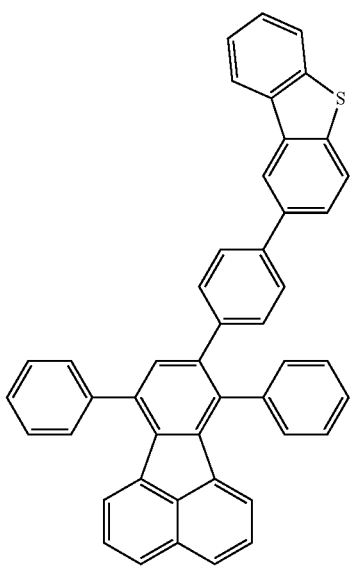
Compound 31
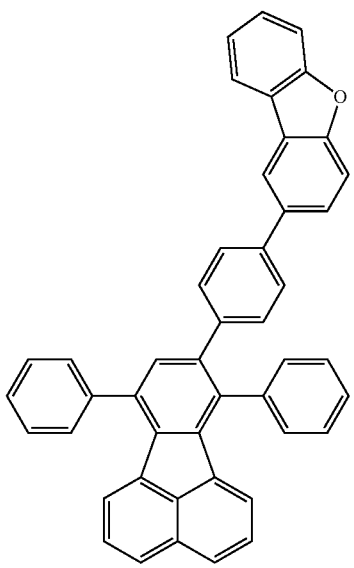

Compound 32
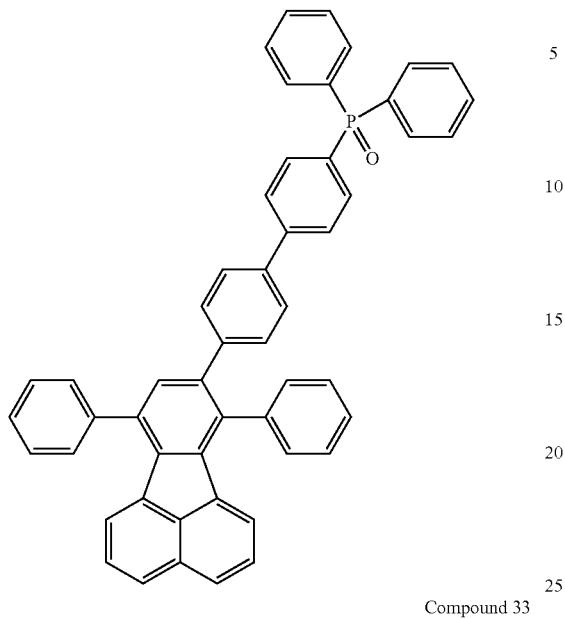
Compound 33
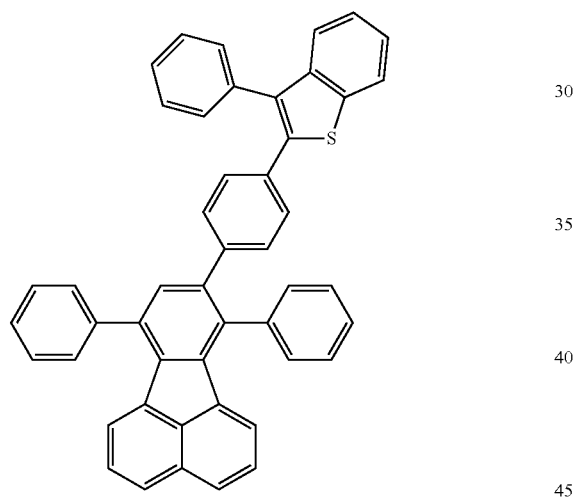
Compound 34
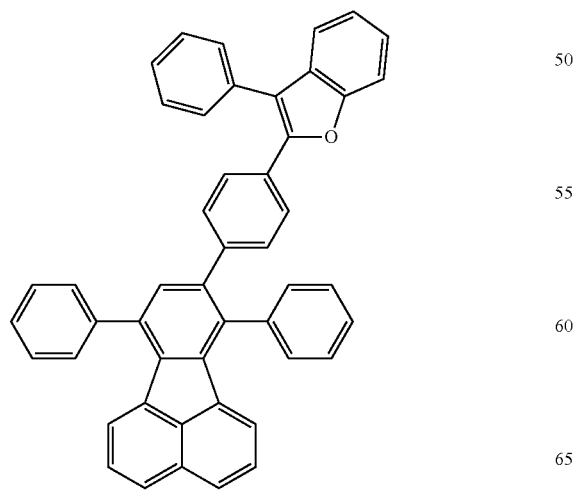
Compound 35
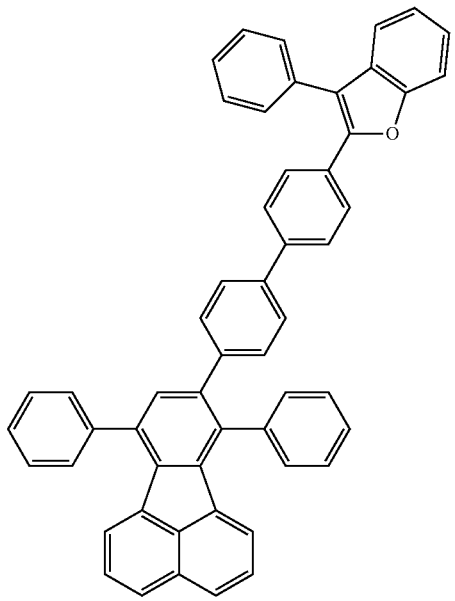
Compound 36
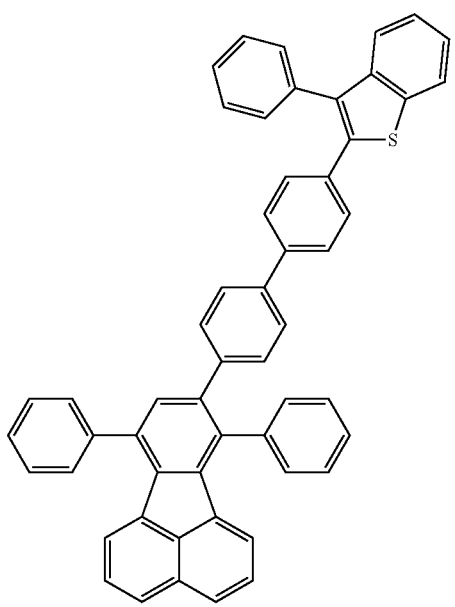

Compound 37

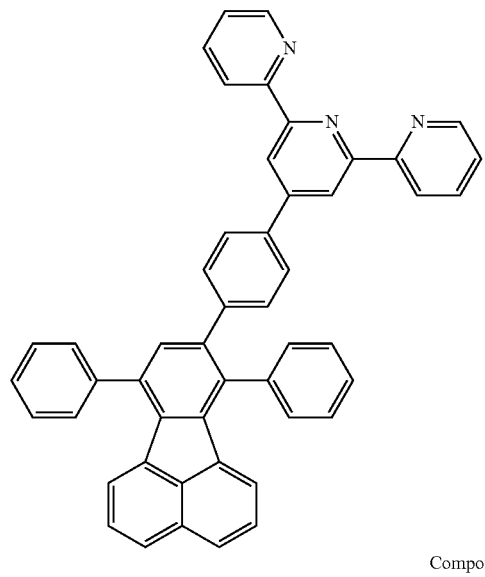

Compound 38

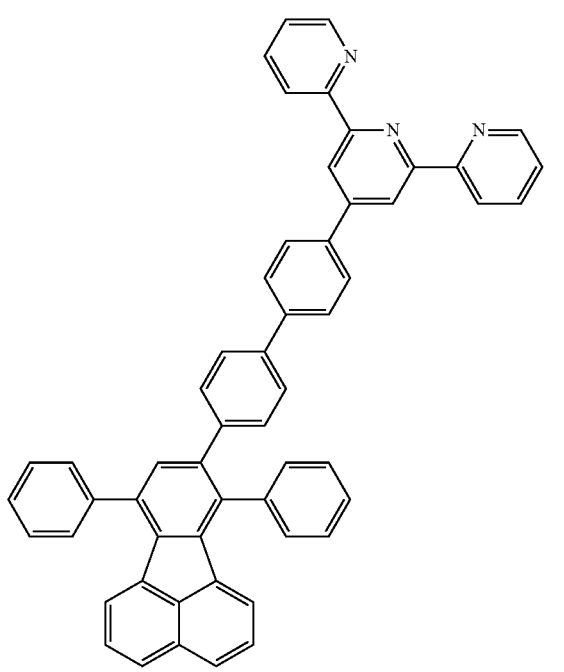

The compound of Chemical Formula 1 may have suitable characteristics for use as an organic material layer used in an organic electronic device by having fluoranthene as the core structure and introducing various substituents, as shown in Chemical Formula 1.

The conjugation length of a compound and the energy band gap have a close relationship. Specifically, the longer the conjugation length is, the smaller the energy band gap is. As described above, the compound core of Chemical Formula 1 includes limited conjugation, therefore, the energy band gap is large.

In the present specification, compounds having various energy band gap values may be synthesized by introducing various substituents at positions R1 to R7 and R' of the core structure having a large energy band gap as above. Typically, adjusting an energy band gap by introducing substituents to a core structure having a large energy band gap is simple, however, when a core structure has a small energy band gap, largely adjusting the energy band gap is difficult by introducing substituents.

In addition, in the present specification, the HOMO and LUMO energy level of the compound may be adjusted by introducing various substituents at positions R1 to R7 and R' of the core structure having the structure as above.

In addition, by introducing various substituents to the core structure having the structure as above, compounds having unique characteristics of the introduced substituents may be synthesized. For example, by introducing substituents normally used in a hole injection layer material, a hole transfer layer material, a light emitting layer material and an electron transfer layer material, which are used in the manufacture of an organic electronic device, to the core structure, materials satisfying the conditions required for each organic material layer may be synthesized.

The compound of Chemical Formula 1 includes fluoranthene in the core structure, thereby has an energy level suitable as a hole injection and/or a hole transfer material in an organic light emitting device. In the present specification, a device having low driving voltage and high light efficiency can be obtained by selecting compounds having suitable energy levels depending on the substituents among the compounds of Chemical Formula 1, and using the compound in an organic light emitting device.

In addition, by introducing various substituents to the core structure, the energy band gap can be finely adjusted, and meanwhile, characteristics at the interface between organic materials are improved, and therefore, the materials can have various applications.

Meanwhile, the compound of Chemical Formula 1 has excellent thermal stability due to its high glass transition temperature ($T_g$). This thermal stability enhancement becomes an important factor that provides a driving stability to a device.

The compound of Chemical Formula 1 may be prepared based on the preparation examples described later.

As the compound of Chemical Formula 1 of the present specification, a compound is synthesized by reacting acenaphthenequinone and substituted propanone. To this synthesized compound, ethynyl benzene to which a substituent is attached is synthesized, and the compound of Chemical Formula 1 is provided.

Alternatively, a compound is synthesized by reacting acenaphthenequinone and substituted propanone, a fluoranthene derivative is synthesized by reacting the compound with substituted ethynyl benzene, and then the compound of Chemical Formula 1 is provided by introducing various substituents to the fluoranthene derivative.

The present specification also provides an organic electronic device that uses the fluoranthene compound.

In one embodiment of the present specification, an organic electronic device provided includes a first electrode, a second electrode, and one or more layers of organic material layers provided between the first electrode and the second electrode, wherein one or more layers of the organic material layers include the fluoranthene compound.

The organic electronic device may be selected from the group consisting of an organic light emitting device, an organic solar cell and an organic transistor.

The organic material layer of the organic electronic device of the present specification may be formed as a monolayer structure, but may be formed as a multilayer structure in which two or more layers of the organic material layers are laminated. For example, the organic light emitting device of the present specification may have a structure including a hole injection layer, a hole transfer layer, a light emitting layer, an electron transfer layer, an electron injection layer, and the like as the organic material layer. However, the structure of the organic light emitting device is not limited thereto, and may include less number of organic material layers.

In another embodiment, the organic electronic device may be a normal-type organic electronic device in which an anode, one or more layers of organic material layers, and a cathode are laminated on a substrate in consecutive order.

In another embodiment, the organic electronic device may be an inverted-type organic electronic device in which a cathode, one or more layers of organic material layers, and an anode are laminated on a substrate in consecutive order.

The organic electronic device of the present specification may be prepared using materials and methods known in the related art except that the compound of the present specification, that is, the fluoranthene compound, is included in one or more layers of organic material layers.

For example, the organic electronic device of the present specification may be manufactured by laminating a first electrode, an organic material layer and a second electrode on a substrate in consecutive order. At this time, the organic electronic device may be manufactured by forming an anode through the deposition of a metal, a metal oxide having conductivity, or alloys thereof on a substrate using a physical vapor deposition (PVD) method such as a sputtering method or an e-beam evaporation method, forming an organic material layer that includes a hole injection layer, a hole transfer layer, a light emitting layer and an electron transfer layer thereon, and then depositing a material that can be used as a cathode thereon. In addition to this method, the organic electronic device may be manufactured by consecutively depositing a cathode material, an organic material layer and an anode material on a substrate.

In addition, when the organic electronic device is manufactured, the fluoranthene compound may be formed as an organic material layer using a solution coating method as well as a vacuum deposition method. Herein, the solution coating method means spin coating, dip coating, doctor blading, ink jet printing, screen printing, a spray method, roll coating or the like, but is not limited thereto.

In one embodiment of the present specification, the organic electronic device may be an organic light emitting device.

In one embodiment of the present specification, an organic light emitting device provided includes a first electrode, a second electrode, and one or more layers of organic material layers including a light emitting layer provided between the first electrode and the second electrode, wherein one or more layers of the organic material layers include the fluoranthene compound.

In one embodiment of the present specification, the organic material layer includes a hole injection layer, a hole transfer layer, or a layer that injects and transfers holes at the same time, and the hole injection layer, the hole transfer layer, or the layer that injects and transfers the holes at the same time includes the fluoranthene compound.

In one embodiment of the present specification, the organic material layer includes an electron transfer layer, an electron injection layer, or a layer that transfers and injects electrons at the same time, and the electron transfer layer, the electron injection layer, or the layer that transfers and injects electrons at the same time includes the fluoranthene compound.

In one embodiment of the present specification, the light emitting layer includes the fluoranthene compound.

In one embodiment of the present specification, the light emitting layer includes the fluoranthene compound as the host of the light emitting layer.

In one embodiment of the present specification, the light emitting layer includes the fluoranthene compound as the host of the light emitting layer, and a dopant may be selected from among dopant materials known in the industry by those skilled in the related art depending on the characteristics required in an organic light emitting device, but is not limited thereto.

In one embodiment of the present specification, the organic light emitting device further includes one, two or more layers selected from the group consisting of a hole injection layer, a hole transfer layer, an electron transfer layer, an electron injection layer, an electron blocking layer and a hole blocking layer.

In another embodiment, the organic material layer of the organic light emitting device may include a hole injection layer or a hole transfer layer including a compound that includes an arylamino group, a carbazole group or a benzocarbazole group, in addition to an organic material layer that includes the fluoranthene compound represented by Chemical Formula 1.

In one embodiment of the present specification, the organic light emitting device may be a top-emission type, a bottom-emission type or a dual-emission type depending on the materials used.

For example, in embodiments of the organic electronic device of the present specification, the organic electronic device may have a structure shown in FIG. 1 and FIG. 2, but the structure is not limited thereto.

FIG. 1 illustrates the structure of an organic electronic device in which a substrate (1), an anode (2), a light emitting layer (3) and a cathode (4) are laminated in consecutive order. In this structure, the fluoranthene compound may be included in the light emitting layer (3).

FIG. 2 illustrates the structure of an organic electronic device in which a substrate (1), an anode (2), a hole injection layer (5), a hole transfer layer (6), a light emitting layer (3), an electron transfer layer (7) and a cathode (4) are laminated in consecutive order. In this structure, the fluoranthene compound may be included in one or more layers of the hole injection layer (5), the hole transfer layer (6), the light emitting layer (3) and the electron transfer layer (7).

In one embodiment of the present specification, the organic electronic device may be an organic solar cell.

In one embodiment of the present specification, an organic solar cell provided includes a first electrode; a second electrode; and one or more layers of organic material layers including a photoactive layer provided between the first electrode and the second electrode, wherein one or more layers of the organic material layers include the fluoranthene compound.

In one embodiment of the present specification, the organic material layer includes an electron transfer layer, an electron injection layer, or a layer that transfers and injects electrons at the same time, and the electron transfer layer, the electron injection layer, or the layer that transfers and injects electrons at the same time includes the fluoranthene compound.

In another embodiment, the photoactive layer may include the fluoranthene compound.

In another embodiment, the organic material layer includes an electron donor and an electron acceptor, and the electron donor or the electron acceptor includes the fluoranthene compound.

In one embodiment of the present specification, when the organic solar cell receives photons from an external light source, electrons and holes are generated between the electron donor and the electron acceptor. The generated holes are transferred to an anode through an electron donor layer.

In one embodiment of the present specification, the organic solar cell may further include additional organic material layers. The organic solar cell may reduce the number of organic material layers by using organic materials simultaneously having a number of functions.

In one embodiment of the present specification, the organic electronic device may be an organic transistor.

In one embodiment of the present specification, an organic transistor provided includes a source, a drain, a gate and one or more layers of organic material layers, wherein one or more layers of the organic material layers include the fluoranthene compound.

In one embodiment of the present specification, the organic transistor may include a charge generation layer, and the charge generation layer may include the fluoranthene compound.

In another embodiment, the organic transistor may include an insulation layer, and the insulation layer may be located on the substrate and the gate.

When the organic electronic device includes a plurality of organic material layers, the organic material layers may be formed with identical materials or different materials.

In one embodiment of the present specification, the first electrode is a cathode, and the second electrode is an anode.

In one embodiment of the present specification, the first electrode is an anode, and the second electrode is a cathode.

The substrate may be selected considering optical properties and physical properties as necessary. For example, the substrate is preferably transparent. Hard materials may be used as the substrate, however, the substrate may be formed with flexible materials such as plastic.

Materials of the substrate include, in addition to glass and quartz, polyethyleneterephthalate (PET), polyethylene naphthalate (PEN), polypropylene (PP), polyimide (PI), polycarbonate (PC), polystyrene (PS), polyoxymethylene (POM), an acrylonitrile styrene (AS) copolymer, an acrylonitrile butadiene styrene (ABS) copolymer, triacetyl cellulose (TAC), polyarylate (PAR), and the like, but are not limited thereto.

As the cathode material, a material having small work function is normally preferable so that electron injection to the organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, or the like, but are not limited thereto.

As the anode material, a material having large work function is normally preferable so that hole injection to the organic material layer is smooth. Specific examples of the anode material that can be used in the present specification include metals such as vanadium, chromium, copper, zinc or gold, or alloys thereof; metal oxides such as zinc oxides, indium oxides, indium tin oxides (ITO) or indium zinc oxides (IZO); and mixtures of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, or the like, but are not limited thereto.

The hole transfer layer is a layer that receives holes from a hole injection layer and transfers the holes to a light emitting layer, and a hole transfer material is a material that can receive holes from an anode or a hole injection layer, move the holes to a light emitting layer, and a material having high mobility for holes is suitable. Specific examples thereof include an arylamine-based organic material, a conductive polymer, a block copolymer having conjugated parts and non-conjugated parts together, and the like, but are not limited thereto.

The hole injection layer is a layer that injects holes from an electrode, and a hole injection material is preferably a compound that has an ability to transfer the holes thereby has a hole injection effect in an anode and has an excellent hole injection effect for a light emitting layer or a light emitting material, prevents the movement of excitons generated in the light emitting layer to an electron injection layer or an electron injection material, and in addition, has excellent thin film forming ability. The highest occupied molecular orbital (HOMO) of the hole injection material is preferably between the work function of an anode and the HOMO of surrounding organic material layers. Specific examples of the hole injection material include a metal porphyrin, oligothiophene, an arylamine-based organic material, a phthalocyanine derivative, a hexanitrile hexazatriphenylene-based organic material, a quinacridone-based organic material, a perylene-based organic material, anthraquinone, and a polyaniline- and polythiophene-based conductive polymer, and the like, but are not limited thereto.

The light emitting material is a material that can emit light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include a 8-hydroxy-quinoline aluminum complex ($Alq_3$); a carbazole-based compound; a dimerized styryl compound; BAlq; a 10-hydroxybenzo quinoline-metal compound; a benzoxazole-, a benzthiazole- and a benzimidazole-based compound; a poly(p-phenylenevinylene) (PPV)-based polymer; a spiro compound; polyfluorene, rubrene or the like, but are not limited thereto.

The light emitting layer may include a host material and a dopant material. The host material includes a fused aromatic ring derivative, a heteroring-containing compound, or the like. Specifically, the fused aromatic ring derivative includes an anthracene derivative, a pyrene derivative, a naphthalene derivative, a pentacene derivative, a phenanthrene compound, a fluoranthene compound or the like, and the heteroring-containing compound includes a carbazole derivative, a dibenzofuran derivative, a ladder-type furan compound, a pyrimidine derivative or the like, but are not limited thereto.

The dopant material includes organic compounds, metals or metal compounds.

The dopant material includes an aromatic amine derivative, a styrylamine compound, a boron complex, a fluoranthene compound, a metal complex, or the like. Specifically, the aromatic amine derivative includes arylamino-including pyrene, anthracene, crycene and periflanthene as the fused aromatic ring derivative having a substituted or unsubstituted arylamino group, and the styrylamine compound includes a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, but the styrylamine compound is not limited thereto. In addition, the metal complex includes an iridium complex, a platinum complex or the like, but is not limited thereto.

The electron transfer layer is a layer that receives electrons from an electron injection layer and transfers the electrons to a light emitting layer, and an electron transfer material is a material that can receive electrons from a cathode, move the electrons to a light emitting layer, and a material having high mobility for electrons is suitable. Specific examples thereof include an Al complex of 8-hydroxyquinoline; a complex including Alq3; an organic radical compound; a hydroxyflavone-metal complex or the like, but are not limited thereto. The electron transfer layer can be used together with any desired cathode material as is used according to technologies in the related art. Particularly, examples of the suitable cathode material are common materials that have small work function, and followed by an aluminum layer or a silver layer. Specifically the cathode material includes cesium, barium, calcium, ytterbium and samarium, and in each case, an aluminum layer or a silver layer follows.

The electron injection layer is a layer that injects electrons from an electrode, and an electron injection material is preferably a compound that has an ability to transfer the electrons, has an electron injection effect in a cathode and has an excellent electron injection effect for a light emitting layer or a light emitting material, prevents the movement of excitons generated in the light emitting layer to the electron injection layer, and in addition, has excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, a metal complex compound, a nitrogen-containing 5-membered ring derivative, or the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)berylium, bis (10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium or the like, but is not limited thereto.

The hole blocking layer is a layer that blocks the arrival of holes in a cathode, and generally, may be formed under the same conditions as those of the hole injection layer. Specific examples thereof include an oxadiazole derivative, a triazole derivative, a phenanthroline derivative, BCP, an aluminum complex or the like, but are not limited thereto.

The electron blocking layer is a layer that improves the probability of electron-hole recombination by receiving holes while blocking electrons, and a material having significantly low electron transfer ability while having hole transfer ability are suitable. As the material of the electron blocking layer, the materials of the hole transfer layer described above may be used as necessary, but the material is not limited thereto, and known electron blocking layers may be used.

The organic electronic device according to the present specification may be a top-emission type, a bottom-emission type or a dual-emission type depending on the materials used.

Hereinafter, a method for preparing the compound represented of Chemical Formula 1 and the manufacture of an organic light emitting device including the same will be described in detail with reference to examples. However, the following examples are for illustrative purposes only, and the scope of the present specification is not limited thereto.

Preparation Example (1) Preparation of [Compound A-1]

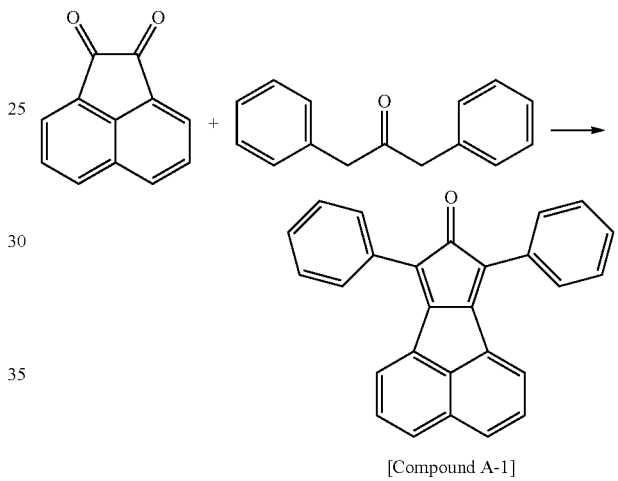

[Compound A-1]

After acenaphthenequinone (30 g, 164 mmol) and 1,3-diphenyl-2-propanone (34 g, 164 mmol) were placed in ethanol (600 mL), potassium hydroxide (KOH) (27.6 g, 492 mmol) was added thereto, and the mixture was stirred under reflux for hours at 85° C. The temperature was lowered to room temperature, 300 mL of water was added thereto, the solid produced was filtered and dried, and [Compound A-1] (45 g, yield 77%) was prepared. MS: $[M+H]^+=357$ (2) Preparation of [Compound A-2]

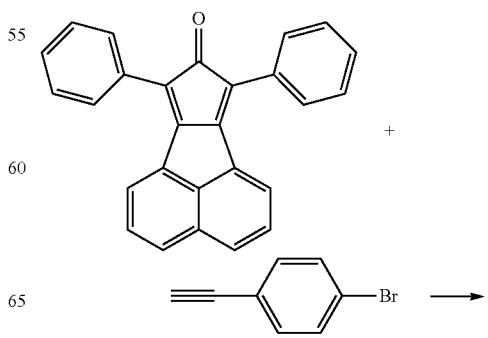

-continued

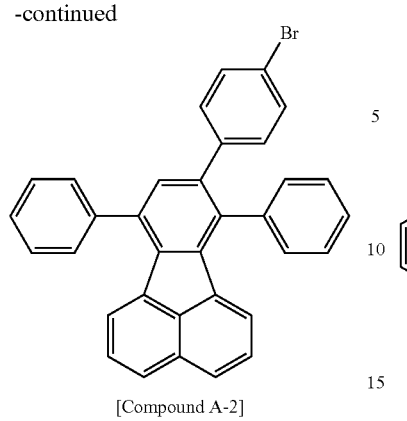

[Compound A-2]

After [Compound A-1] (30 g, 84.2 mmol) and 1-bromo-4-ethynylbenzene (16.8 g, 92.8 mmol) were placed in xylene (500 mL), the mixture was stirred under reflux for 48 hours at 140° C. The temperature was lowered to room temperature, 300 mL of ethanol was added thereto, the solid produced was filtered and dried, and [Compound A-2] (31.3 g, yield 74%) was prepared. MS: [M+H]$^+$=510

(3) Preparation of [Compound A-3]

[Compound A-3]

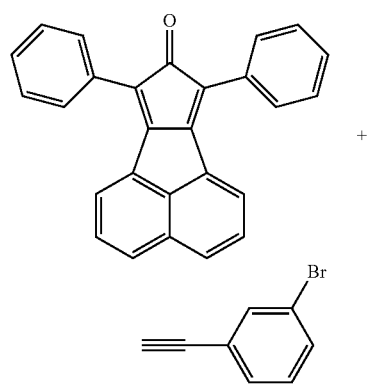

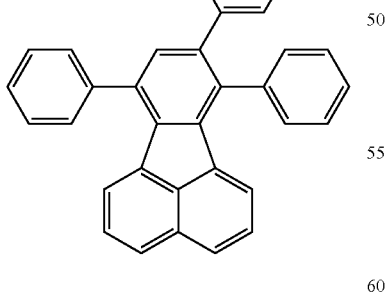

After [Compound A-1] (30 g, 84.2 mmol) and 1-bromo-4-ethynylbenzene (16.8 g, 92.8 mmol) were placed in xylene (500 mL), the mixture was stirred under reflux for 48 hours at 140° C. The temperature was lowered to room temperature, 300 mL of ethanol was added thereto, the solid produced was filtered and dried, and [Compound A-2] (29.7 g, yield 69%) was prepared. MS: [M+H]$^+$=510

(4) Preparation of [Compound B-1]

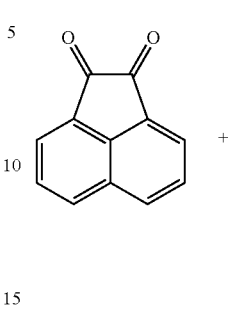

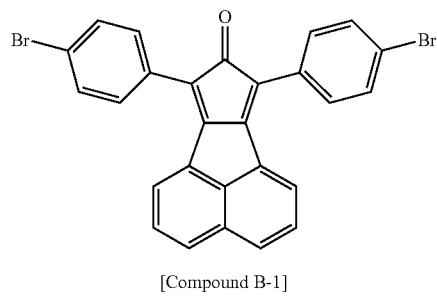

[Compound B-1]

After acenaphthenequinone (6.9 g, 38 mmol) and 1,3-bis(4-bromophenyl)propan-2-one (14 g, 38 mmol) were placed in ethanol (300 mL), potassium hydroxide (KOH) (6.4 g, 114 mmol) was added thereto, and the mixture was stirred under reflux for 48 hours at 85° C. The temperature was lowered to room temperature, 200 mL of water was added thereto, the solid produced was filtered and dried, and [Compound B-1] (17.3 g, yield 88%) was prepared. MS: [M+H]$^+$=515

(5) Preparation of [Compound B-2]

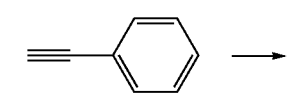

-continued

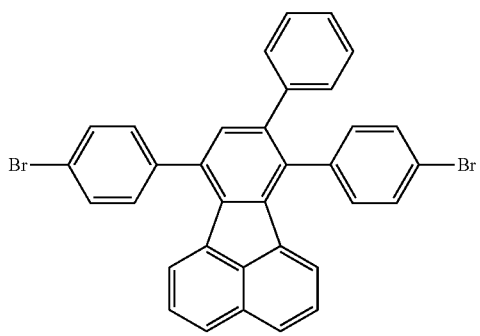

[Compound B-2]

After [Compound B-1] (17.3 g, 33.6 mmol) and ethynylbenzene (4.1 g, 40.3 mmol) were placed in xylene (200 mL), the mixture was stirred under reflux for 48 hours at 140° C. The temperature was lowered to room temperature, 200 mL of ethanol was added thereto, the solid produced was filtered and dried, and [Compound B-2] (14.3 g, yield 72%) was prepared. MS: [M+H]$^+$=589

(6) Preparation of [Compound C-1]

[Compound C-1]

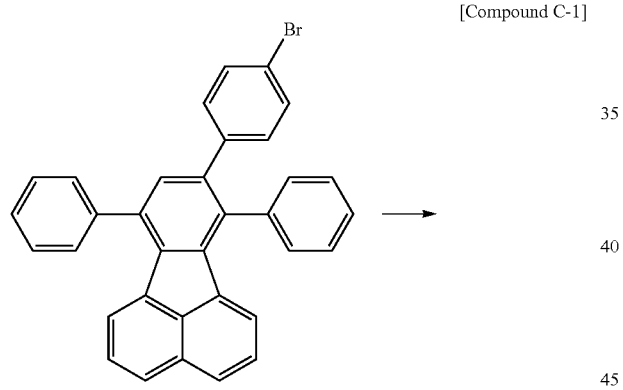

→

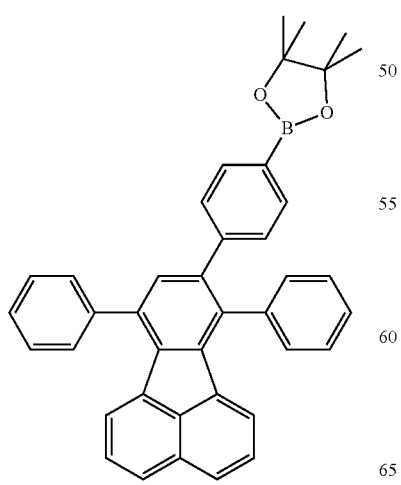

After [Compound A-2] (30 g, 58.9 mmol) and bis(pinacolato)diboron (16.5 g, 64.8 mmol) were placed in dioxane (300 mL), potassium acetate (17.3 g, 177 mmol) and then Pd(dppf)Cl$_2$CH$_2$Cl$_2$ (0.96 g, 2 mol %) were added thereto, and the mixture was stirred under reflux for 6 hours. The temperature was lowered to room temperature, and the result was filtered. After the filtrate was vacuum distilled and dissolved in chloroform, the result was recrystallized using ethanol, filtered and dried, and [Compound C-1] (27.2 g, yield 83%) was prepared. MS: [M+H]$^+$=557

(7) Preparation of [Compound C-2]

[Compound C-2]

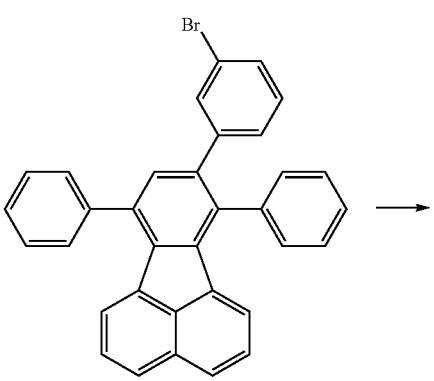

→

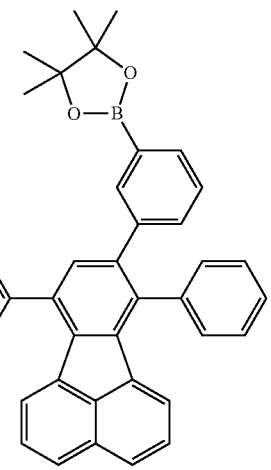

After [Compound A-3] (30 g, 58.9 mmol) and bis(pinacolato)diboron (16.5 g, 64.8 mmol) were placed in dioxane (300 mL), potassium acetate (17.3 g, 177 mmol) and then Pd(dppf)Cl$_2$CH$_2$Cl$_2$ (0.96 g, 2 mol %) were added thereto, and the mixture was stirred under reflux for 6 hours. The temperature was lowered to room temperature, and the result was filtered. After the filtrate was vacuum distilled and dissolved in chloroform, the result was recrystallized using ethanol, filtered and dried, and [Compound C-2] (26.2 g, yield 80%) was prepared. MS: [M+H]$^+$=557

EXAMPLES

Example 1

Preparation of [Compound 2]

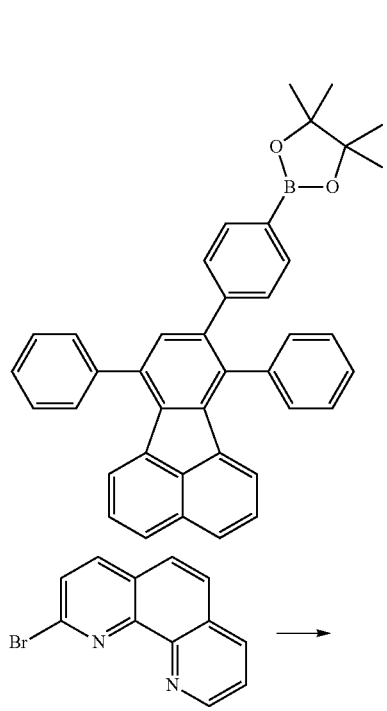

[Compound 2]

+

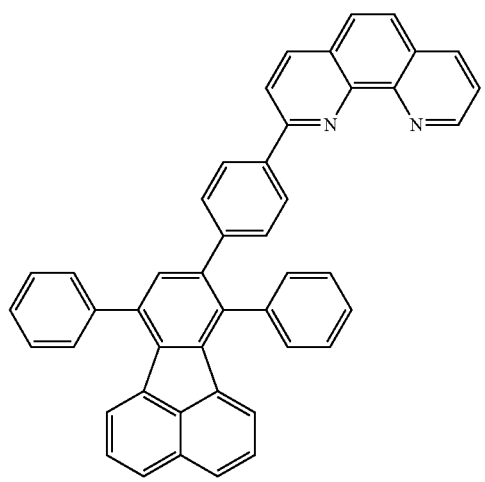

After [Compound C-1] (17.6 g, 31.6 mmol) and 2-bromo-1,10-phenanthroline (8.2 g, 31.6 mmol) were placed in tetrahydrofuran (THF) (200 mL), a 2M aqueous potassium carbonate ($K_2CO_3$) solution (100 mL) and then $Pd(PPh_3)_4$ (0.67 g, mol %) were added thereto, and the mixture was stirred under reflux for 4 hours. The temperature was lowered to room temperature, and the solid produced was filtered. The filtered solid was recrystallized using chloroform and ethanol, then filtered and dried, and [Compound 2] (16.5 g, yield 86%) was prepared. MS: $[M+H]^+=609$

Example 2

Preparation of [Compound 6]

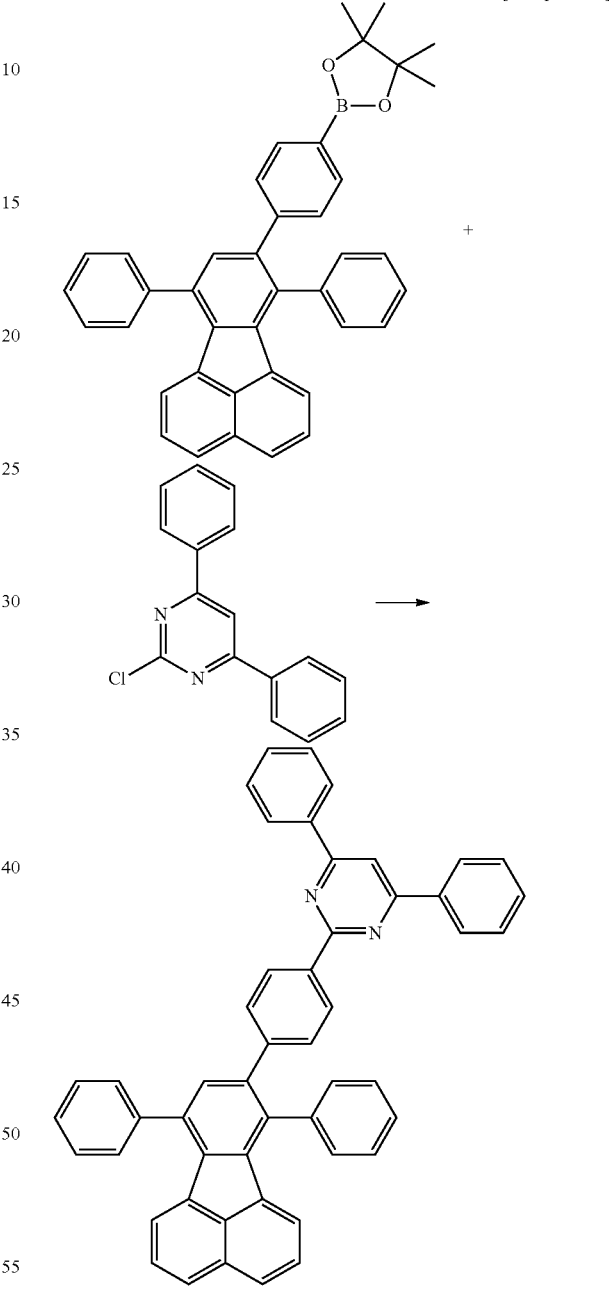

After [Compound C-1] (17.6 g, 31.6 mmol) and 2-chloro-4,6-diphenylpyrimidine (8.4 g, 31.6 mmol) were placed in tetrahydrofuran (THF) (200 mL), a 2M aqueous potassium carbonate ($K_2CO_3$) solution (100 mL) and then $Pd(PPh_3)_4$ (0.67 g, mol %) were added thereto, and the mixture was stirred under reflux for 4 hours. The temperature was lowered to room temperature, and the solid produced was filtered. The filtered solid was recrystallized using chloroform and ethanol, then filtered and dried, and [Compound 6] (15.6 g, yield 75%) was prepared. MS: $[M+H]^+=661$

Example 3

Preparation of [Compound 7]

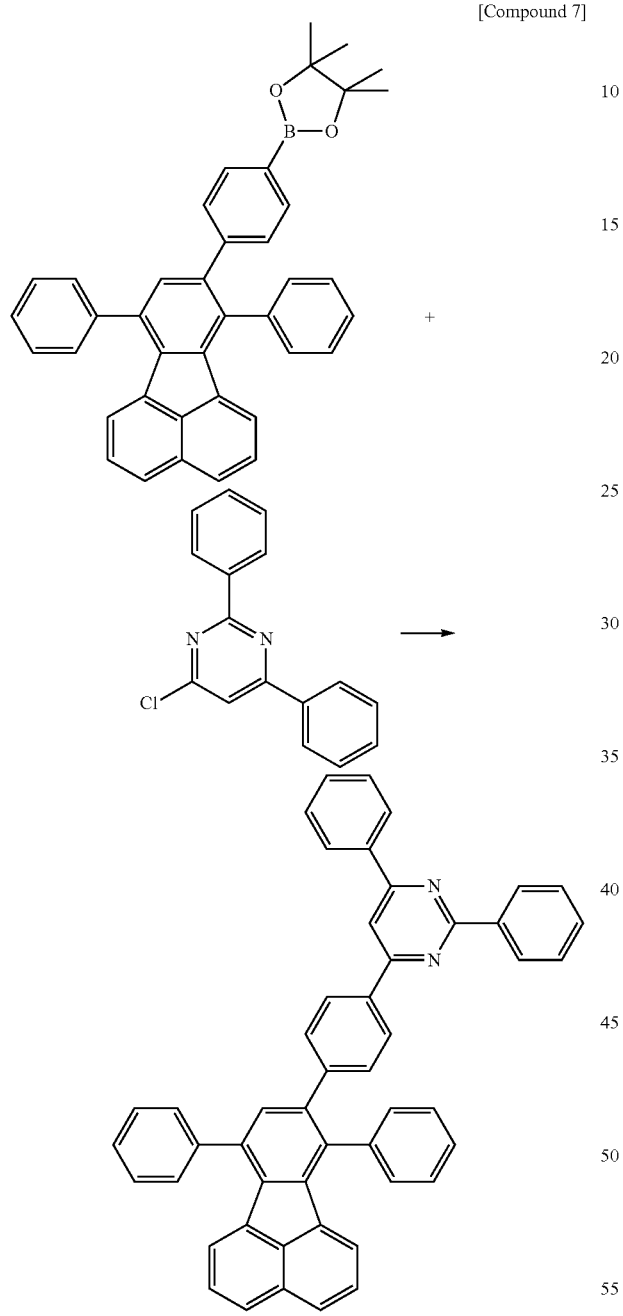

After [Compound C-1] (17.6 g, 31.6 mmol) and 4-chloro-2,6-diphenylpyrimidine (8.4 g, 31.6 mmol) were placed in tetrahydrofuran (THF) (200 mL), a 2M aqueous potassium carbonate ($K_2CO_3$) solution (100 mL) and then $Pd(PPh_3)_4$ (0.67 g, mol %) were added thereto, and the mixture was stirred under reflux for 4 hours. The temperature was lowered to room temperature, and the solid produced was filtered. The filtered solid was recrystallized using chloroform and ethanol, then filtered and dried, and [Compound 7] (14.6 g, yield 70%) was prepared. MS: $[M+H]^+=661$

Example 4

Preparation of [Compound 8]

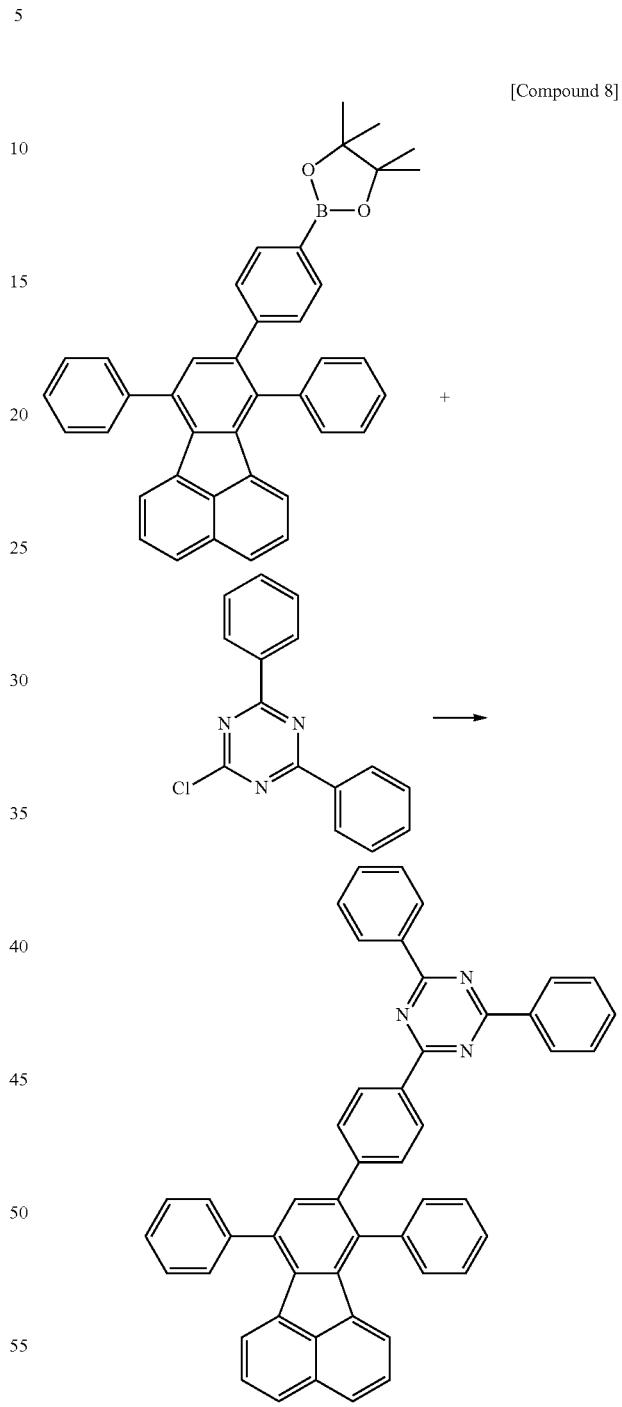

After [Compound C-1] (17.6 g, 31.6 mmol) and 2-chloro-4,6-diphenyl-1,3,5-triazine (8.4 g, 31.6 mmol) were placed in tetrahydrofuran (THF) (200 mL), a 2M aqueous potassium carbonate ($K_2CO_3$) solution (100 mL) and then $Pd(PPh_3)_4$ (0.67 g, mol %) were added thereto, and the mixture was stirred under reflux for 4 hours. The temperature was lowered to room temperature, and the solid produced was filtered. The filtered solid was recrystallized using chloroform and ethanol, then filtered and dried, and [Compound 8] (16.1 g, yield 77%) was prepared. MS: [M+H]$^+$=662

Example 5

Preparation of [Compound 26]

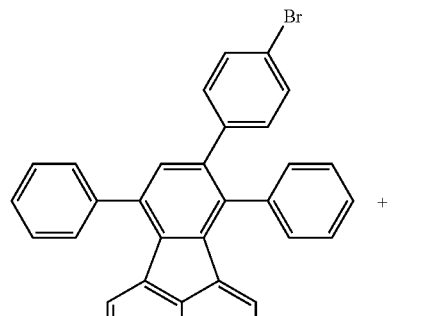

[Compound 26]

After [Compound A-2] (15 g, 29.4 mmol) and 4-dibenzothiophene boronic acid (6.7 g, 29.4 mmol) were placed in tetrahydrofuran (THF) (200 mL), a 2M aqueous potassium carbonate (K$_2$CO$_3$) solution (100 mL) and then Pd(PPh$_3$)$_4$ (0.67 g, mol %) were added thereto, and the mixture was stirred under reflux for 4 hours. The temperature was lowered to room temperature, and the solid produced was filtered. The filtered solid was recrystallized using chloroform and ethanol, then filtered and dried, and [Compound 26] (12.6 g, yield 70%) was prepared. MS: [M+H]$^+$=613

Example 6

Preparation of [Compound 27]

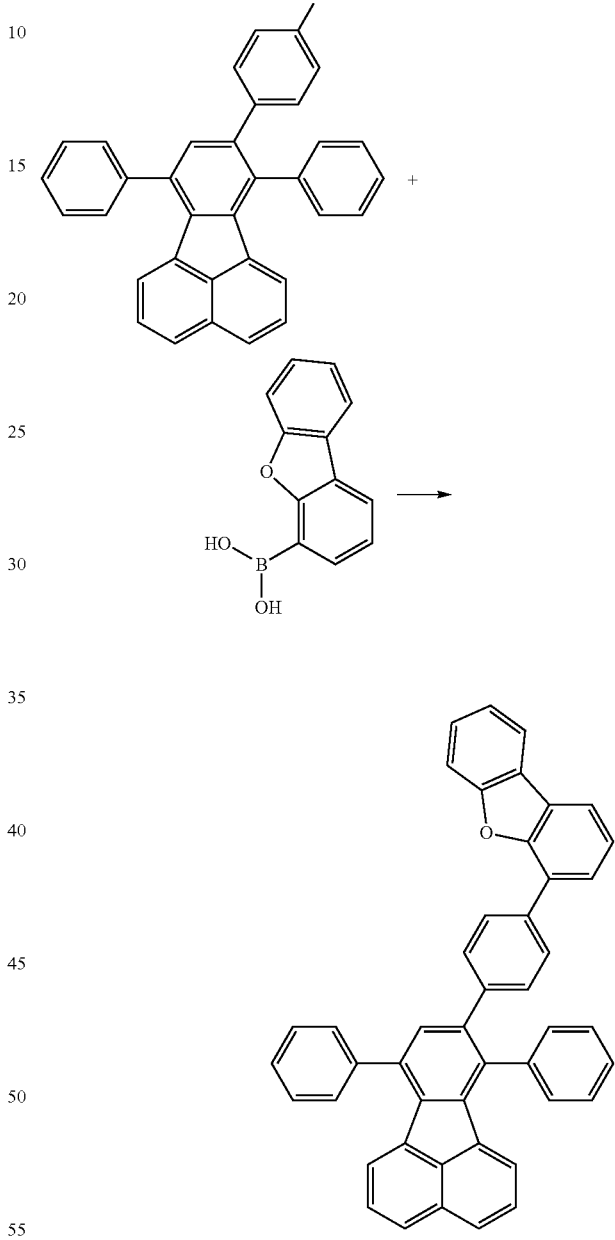

[Compound 27]

After [Compound A-2] (15 g, 29.4 mmol) and 4-dibenzofuran boronic acid (6.2 g, 29.4 mmol) were placed in tetrahydrofuran (THF) (200 mL), a 2M aqueous potassium carbonate (K$_2$CO$_3$) solution (100 mL) and then Pd(PPh$_3$)$_4$ (0.67 g, mol %) were added thereto, and the mixture was stirred under reflux for 4 hours. The temperature was lowered to room temperature, and the solid produced was filtered. The filtered solid was recrystallized using chloroform and ethanol, then filtered and dried, and [Compound 27] (13.5 g, yield 77%) was prepared. MS: [M+H]$^+$=597

Example 7

Preparation of [Compound 11]

[Compound 11]

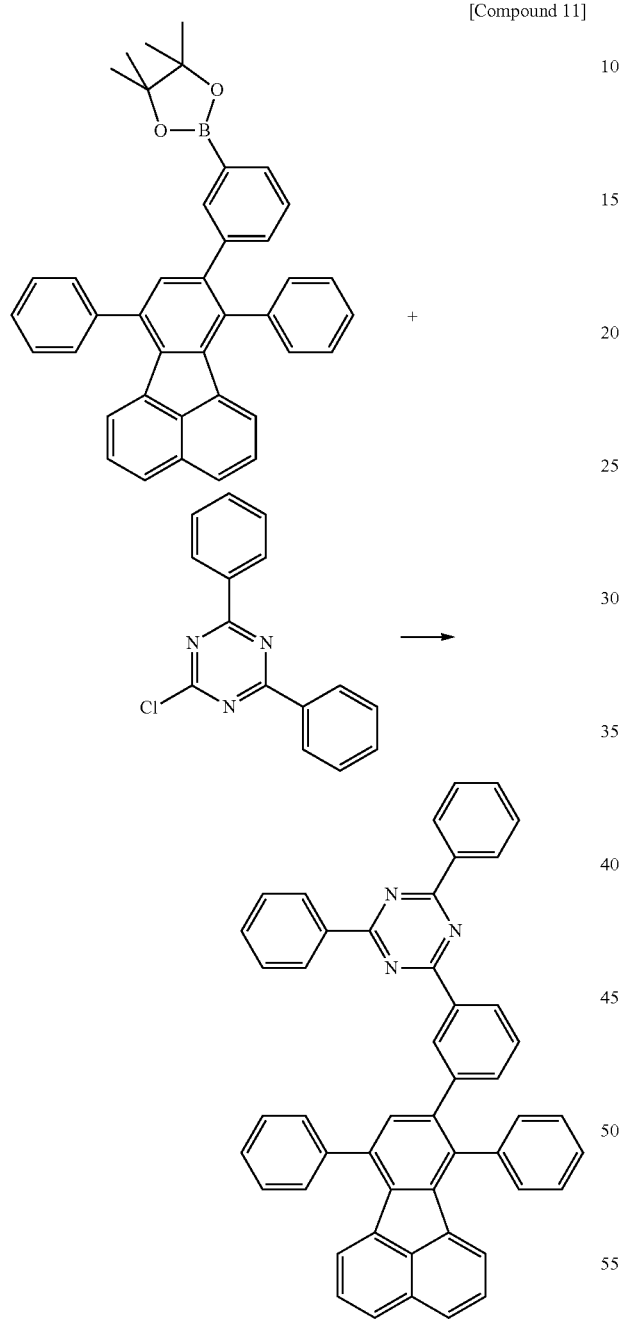

After [Compound C-2] (15 g, 26.8 mmol) and 2-chloro-4,6-diphenyl-1,3,5-triazine (7.16 g, 26.8 mmol) were placed in tetrahydrofuran (THF) (200 mL), a 2M aqueous potassium carbonate (K₂CO₃) solution (100 mL) and then Pd(PPh₃)₄ (0.67 g, mol %) were added thereto, and the mixture was stirred under reflux for 4 hours. The temperature was lowered to room temperature, and the solid produced was filtered. The filtered solid was recrystallized using chloroform and ethanol, then filtered and dried, and [Compound 11] (13.3 g, yield 75%) was prepared. MS: [M+H]⁺=661

Example 8

Preparation of [Compound 24]

[Compound 24]

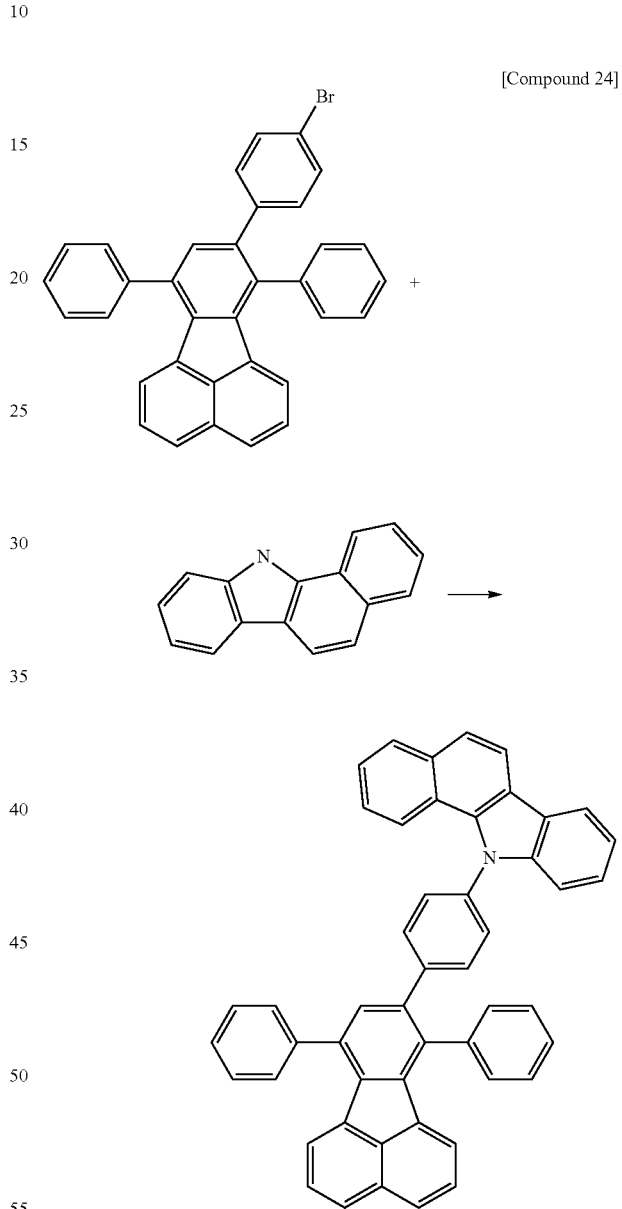

After [Compound A-2] (15 g, 29.5 mmol) and 11H-benzo[a]carbazole (6.4 g, 29.5 mmol) were placed in toluene (150 mL), sodium tetrabutoxide (NaOtBu) (15 g) and then Pd(PtBu₄)₂ (0.16 g, 1 mol %) were added thereto, and the mixture was stirred under reflux for 4 hours. The temperature was lowered to room temperature, and the solid produced was filtered. The filtered solid was recrystallized using chloroform and ethanol, then filtered and dried, and [Compound 24] (11.4 g, yield 60%) was prepared. MS: [M+H]⁺=645

Example 9

Preparation of [Compound 32]

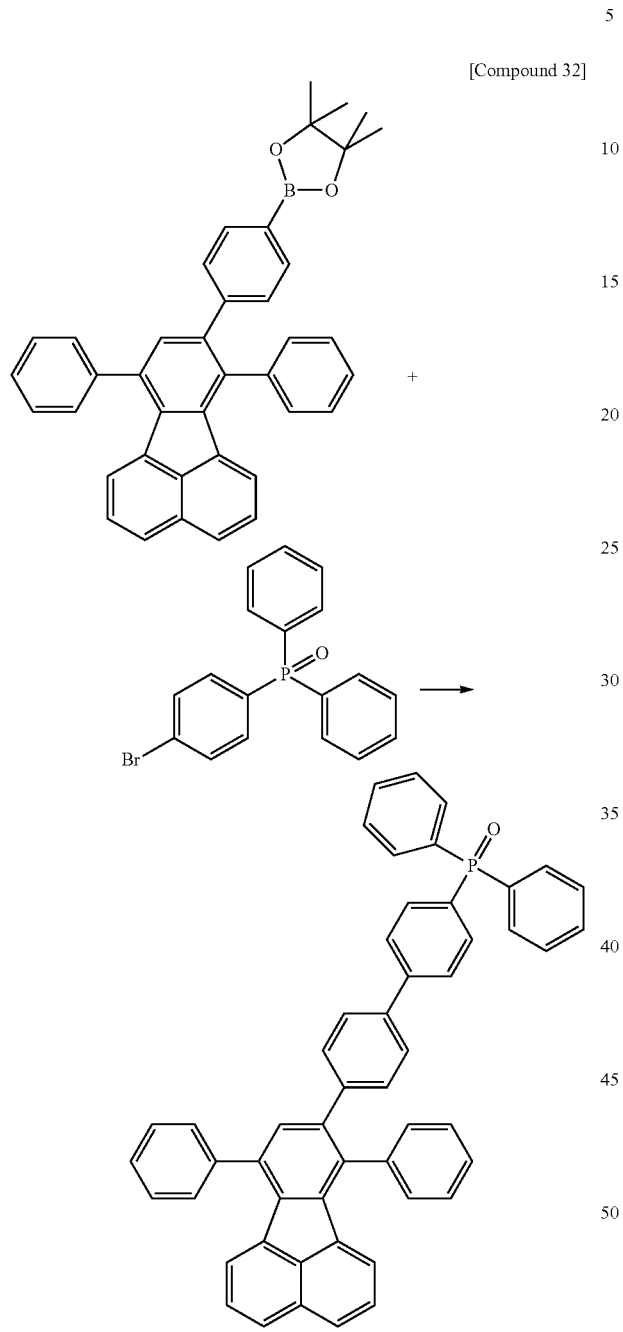

[Compound 32]

After [Compound C-1] (18.0 g, 32.4 mmol) and (4-bromophenyl)diphenylphosphineoxide (11.6 g, 32.4 mmol) were placed in tetrahydrofuran (THF) (200 mL), a 2M aqueous potassium carbonate ($K_2CO_3$) solution (100 mL) and then $Pd(PPh_3)_4$ (0.75 g, 2 mol %) were added thereto, and the mixture was stirred under reflux for 4 hours. The temperature was lowered to room temperature, and the solid produced was filtered. The filtered solid was recrystallized using chloroform and ethanol, then filtered and dried, and [Compound 32] (13.7 g, yield 64%) was prepared. MS: $[M+H]^+=706$

Example 10

Preparation of [Compound 38]

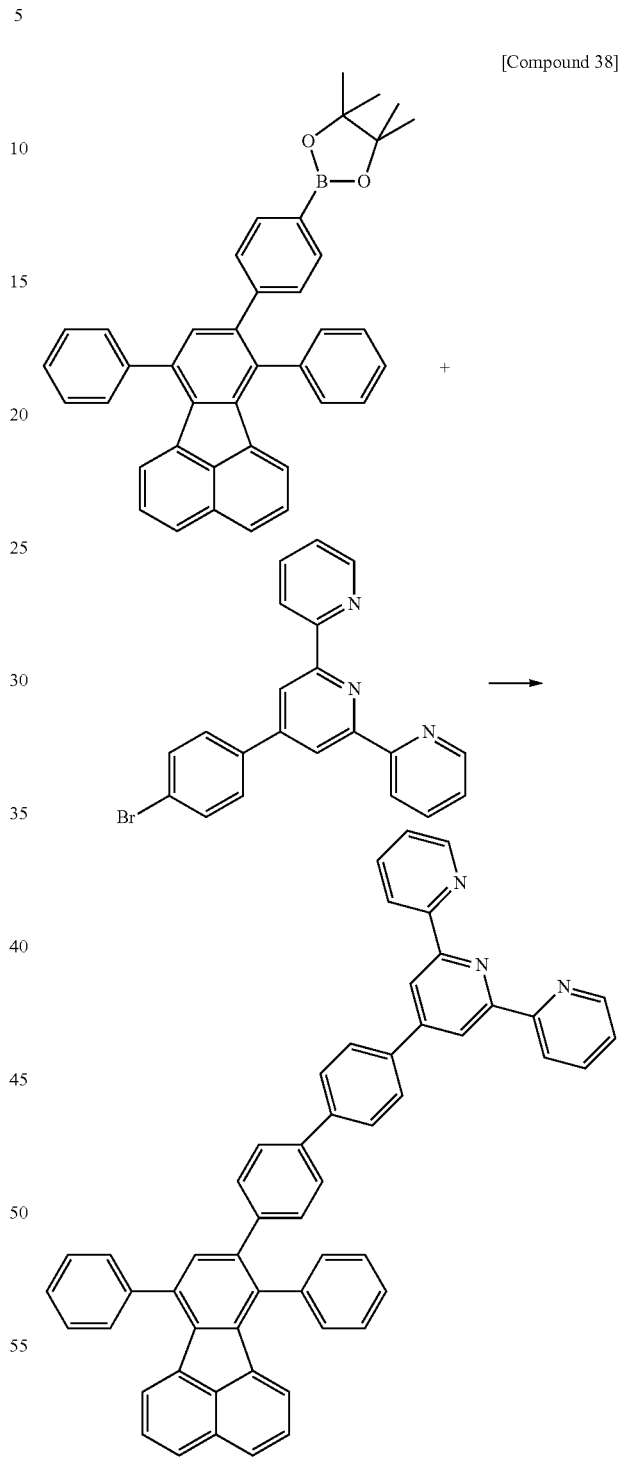

[Compound 38]

After [Compound C-1] (15.0 g, 27.0 mmol) and 4'-(4-bromophenyl)-2,2':6',2''-terpyridine (10.5 g, 27.0 mmol) were placed in tetrahydrofuran (THF) (200 mL), a 2M aqueous potassium carbonate ($K_2CO_3$) solution (100 mL) and $Pd(PPh_3)_4$ (0.62 g, 2 mol %) were added thereto, and the mixture was stirred under reflux for 4 hours. The temperature was lowered to room temperature, and the solid produced was filtered. The filtered solid was recrystallized using chloroform and ethanol, then filtered and dried, and [Compound 38] (15.5 g, yield 78%) was prepared. MS: $[M+H]^+$=737

EXPERIMENTAL EXAMPLE

Manufacture of Organic Light Emitting Device and Characteristics Measurements Thereof Experimental Example 1-1

A glass substrate on which indium tin oxide (ITO) was coated as a thin film to a thickness of 500 Å was placed in distilled water in which a detergent is dissolved, and then was ultrasonic cleaned. At this time, a product of Fischer Corporation was used as the detergent, and as the distilled water, distilled water filtered twice with a filter manufactured by Millipore Corporation was used. After the ITO was cleaned for 30 minutes, ultrasonic cleaning was repeated twice for 10 minutes using distilled water. After the cleaning with distilled water was finished, ultrasonic cleaning was performed using an isopropyl alcohol, acetone and methanol solvent, and the substrate was dried and transferred to a plasma washer. In addition, the substrate was washed for 5 minutes using oxygen plasma, and transferred to a vacuum deposition apparatus.

On the transparent ITO electrode prepared as above, a hole injection layer was formed to a thickness of 100 Å by thermal vacuum depositing hexanitrile hexazatriphenylene (HAT) of the following chemical formula.

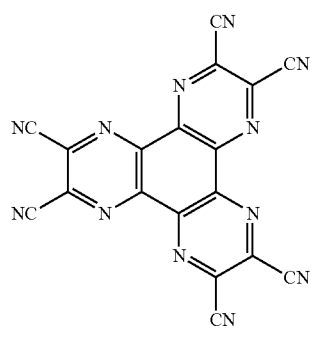

[HAT]

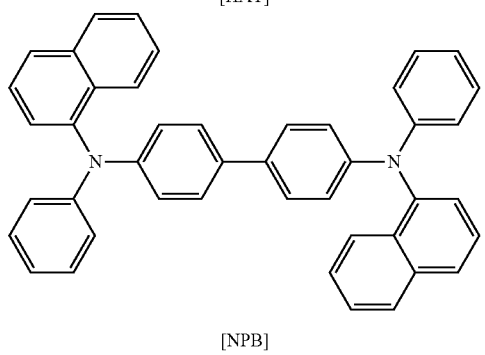

[NPB]

On the hole injection layer, a hole transfer layer was formed by vacuum depositing 4-4'-bis[N-(1-naphthyl)-N-phenylamino]biphenyl (NPB) (1,000 Å) of the chemical formula above.

Subsequently, a light emitting layer was formed on the hole transfer layer to a film thickness of 230 Å by vacuum depositing the following GH and GD in the weight ratio of 10:1.

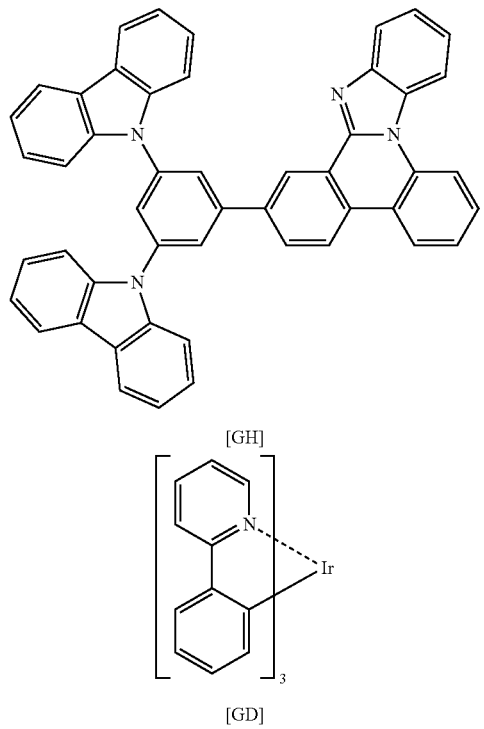

[GH]

[GD]

On the light emitting layer, an electron injection and transfer layer was formed to a film thickness of 350 Å by vacuum depositing [Compound 2].

A cathode was formed on the electron injection and transfer layer by depositing lithium fluoride (LiF) to a thickness of 15 Å and aluminum to a thickness of 2,000 Å in consecutive order.

In the above process, the deposition rate of the organic material was maintained to be 0.4 to 0.7 Å/sec, the deposition rate of the lithium fluoride of the cathode to be 0.3 Å/sec, and the deposition rate of the aluminum to be 2 Å/sec, and the degree of vacuum when being deposited was maintained to be $2\times10^{-7}$ to $5\times10^{-8}$ torr, and as a result, the organic light emitting device was manufactured.

Experimental Example 1-2

The organic light emitting device was manufactured using the same method as in Experimental Example 1-1 except that [Compound 8] was used instead of [Compound 2] in Experimental Example 1-1.

Experimental Example 1-3

The organic light emitting device was manufactured using the same method as in Experimental Example 1-1 except that [Compound 11] was used instead of [Compound 2] in Experimental Example 1-1.

Experimental Example 1-4

The organic light emitting device was manufactured using the same method as in Experimental Example 1-1 except that [Compound 32] was used instead of [Compound 2] in Experimental Example 1-1.

Experimental Example 1-5

The organic light emitting device was manufactured using the same method as in Experimental Example 1-1 except that [Compound 38] was used instead of [Compound 2] in Experimental Example 1-1.

Comparative Example 1

The organic light emitting device was manufactured using the same method as in Experimental Example 1-1 except that the compound of the following Chemical Formula ET-B was used instead of [Compound 2] in Experimental Example 1-1.

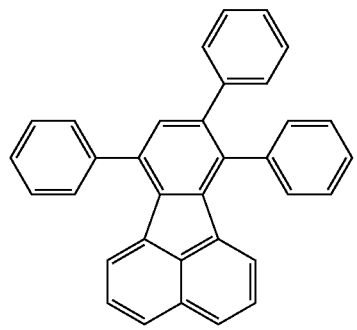

[ET-B]

When current (10 mA/cm$^2$) was applied to the organic light emitting device manufactured by Experimental Example 1-1 to Experimental Example 1-5, and Comparative Example 1, the results of Table 1 were obtained.

TABLE 1

|  | Compound | Voltage (V) | Efficiency (cd/A) | Color Coordinates (x, y) |
| --- | --- | --- | --- | --- |
| Experimental Example 1-1 | 2 | 3.71 | 41.25 | (0.374, 0.621) |
| Experimental Example 1-2 | 8 | 4.15 | 39.11 | (0.374, 0.621) |
| Experimental Example 1-3 | 11 | 4.10 | 40.20 | (0.374, 0.620) |
| Experimental Example 1-4 | 32 | 4.50 | 37.25 | (0.373, 0.618) |
| Experimental Example 1-5 | 38 | 3.63 | 43.55 | (0.373, 0.618) |
| Comparative Example 1 | ET-B | 5.51 | 25.53 | (0.373, 0.617) |

Experimental Example 2-1

On the transparent ITO electrode prepared as in Experimental Example 1-1, a hole injection layer was formed to a thickness of 100 Å by thermal vacuum depositing hexanitrile hexazatriphenylene (HAT) of the chemical formula above.

On the hole injection layer, a hole transfer layer was formed by vacuum depositing 4-4'-bis[N-(1-naphthyl)-N-phenylamino]biphenyl (NPB) (700 Å), hexanitrile hexazatriphenylene (HAT) (50 Å) and 4-4'-bis[N-(1-naphthyl)-N-phenylamino]biphenyl (NPB) (700 Å) of the chemical formula above in consecutive order.

Subsequently, a light emitting layer was formed on the hole transfer layer to a film thickness of 200 Å by vacuum depositing the following BH and BD in the weight ratio of 25:1.

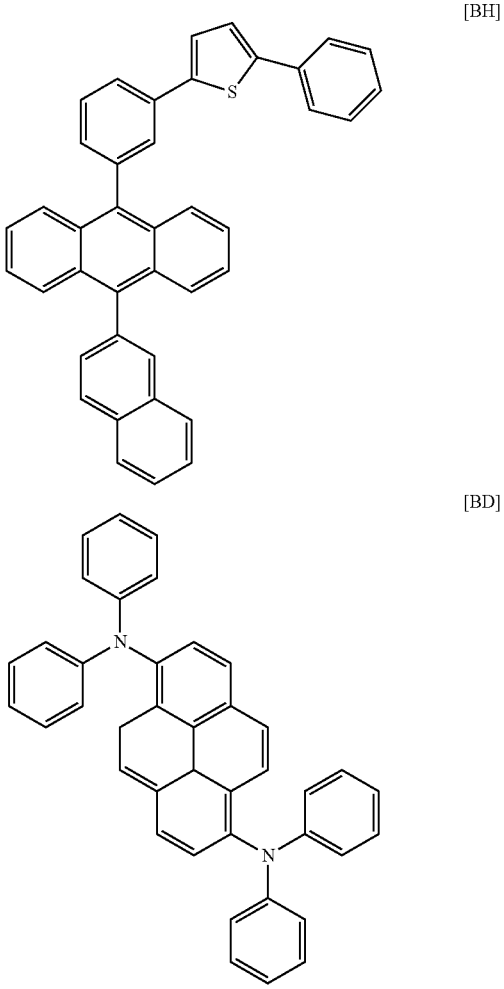

On the light emitting layer, an electron injection and transfer layer was formed to a thickness of 300 Å by vacuum depositing [Compound 7] and the lithium quinolate (LiQ) of the following chemical formula in the weight ratio of 1:1.

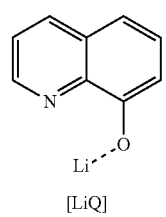

[LiQ]

A cathode was formed on the electron injection and transfer layer by depositing lithium fluoride (LiF) to a thickness of 15 Å and aluminum to a thickness of 2,000 Å in consecutive order.

In the above process, the deposition rate of the organic material was maintained to be 0.4 to 0.7 Å/sec, the deposition rate of the lithium fluoride of the cathode to be 0.3

Å/sec, and the deposition rate of the aluminum to be 2 Å/sec, and the degree of vacuum when being deposited was maintained to be $2\times10^{-7}$ to $5\times10^{-8}$ torr, and as a result, the organic light emitting device was manufactured.

Experimental Example 2-2

The organic light emitting device was manufactured using the same method as in Experimental Example 2-1 except that [Compound 2] was used instead of [Compound 7] in Experimental Example 2-1.

Experimental Example 2-3

The organic light emitting device was manufactured using the same method as in Experimental Example 2-1 except that [Compound 27] was used instead of [Compound 7] in Experimental Example 2-1.

Experimental Example 2-4

The organic light emitting device was manufactured using the same method as in Experimental Example 2-1 except that [Compound 38] was used instead of [Compound 7] in Experimental Example 2-1.

Comparative Example 2

The organic light emitting device was manufactured using the same method as in Experimental Example 2-1 except that the compound of the following Chemical Formula ET-C was used instead of [Compound 7] in Experimental Example 2-1.

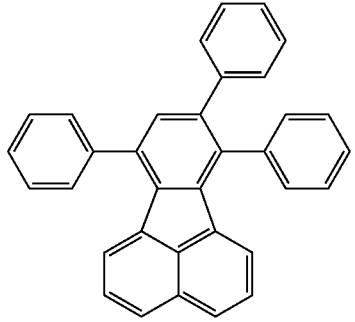

[ET-C]

When current (10 mA/cm²) was applied to the organic light emitting device manufactured by Experimental Examples 2-1 to 2-4 and Comparative Example 2, the results of Table 2 were obtained.

TABLE 2

| | Compound | Voltage (V) | Efficiency (cd/A) | Color Coordinates (x, y) |
|---|---|---|---|---|
| Experimental Example 2-1 | 7 | 4.35 | 6.43 | (0.133, 0.154) |
| Experimental Example 2-2 | 2 | 4.10 | 6.33 | (0.133, 0.153) |
| Experimental Example 2-3 | 27 | 4.51 | 5.99 | (0.133, 0.153) |
| Experimental Example 2-4 | 38 | 4.22 | 6.25 | (0.134, 0.154) |

TABLE 2-continued

| | Compound | Voltage (V) | Efficiency (cd/A) | Color Coordinates (x, y) |
|---|---|---|---|---|
| Comparative Example 2 | ET-C | 5.21 | 5.51 | (0.134, 0.153) |

From the results of Table 2, it can be seen that the novel compound according to the present specification can be used as the material of an organic material layer of an organic electronic device including an organic light emitting device, and an organic electronic device including an organic light emitting device, which uses the novel compound, shows excellent characteristics in efficiency, driving voltage, stability, and the like. In particular, the novel compound according to the present specification has excellent thermal stability, deep HOMO level and hole stability thereby shows excellent characteristics. The novel compound can be used in an organic electronic device including an organic light emitting device either alone or by being mixed with an n-type dopant such as LiQ. The novel compound according to the present specification improves the efficiency, and improves the stability of a device due to the thermal stability of the compound.

REFERENCES

1: Substrate
2: Anode
3: Light Emitting Layer
4: Cathode
5: Hole Injection Layer
6: Hole Transfer Layer
7: Electron Transfer Layer

The invention claimed is:
1. A fluoranthene compound of Chemical Formula 1:

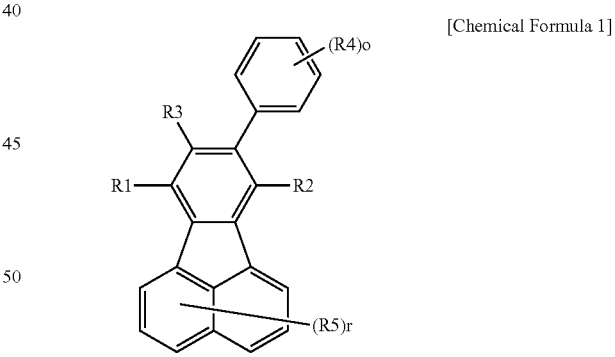

[Chemical Formula 1]

wherein, in Chemical Formula 1:
R1 to R3 are groups having the formula -(L)p-(Y)q;
p is an integer of 0 to 10 and q is an integer of 1 to 10;
o is an integer of 1 to 5;
r is an integer of 0 to 6;
L is a substituted or unsubstituted arylene group, a substituted or unsubstituted alkenylene group, a substituted or unsubstituted fluorenylene group, or a substituted or unsubstituted heteroarylene group having O, N, S or P as a heteroatom;
Y is hydrogen, deuterium, a halogen group, a nitrile group, a nitro group, a hydroxy group, a substituted or unsubstituted alkyl group, a substituted or unsubstituted cycloalkyl group, a substituted or unsubstituted alkoxy group, a substituted or unsubstituted phosphine oxide group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, a substituted or unsubstituted fluorenyl group, a substituted or unsubstituted carbazole group, or a substituted or unsubstituted heteroring group including one or more of N, O, S and P atoms, when p≥2 or q≥2, Ls or Ys are the same as or different from each other;

R1 and R3 may be bonded to each other to form an aliphatic ring, an aromatic ring, an aliphatic heteroring or an aromatic heteroring, or form a spiro bond;

when o≥ 2, R4s are the same as or different from each other;

R4 is:
  (a) a phenyl group substituted with at least one of the following substituents:

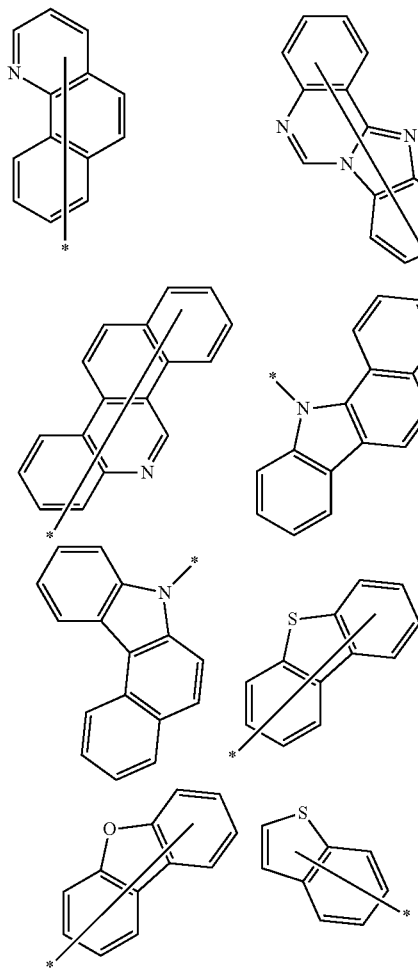

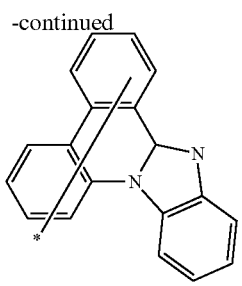

wherein the substituents in the table above are unsubstituted or additionally substituted with substituents selected from the group consisting of an alkyl group, an aryl group, and a heteroring group including one or more of N, O, S or P atoms; or (b) at least one of the following substituents:

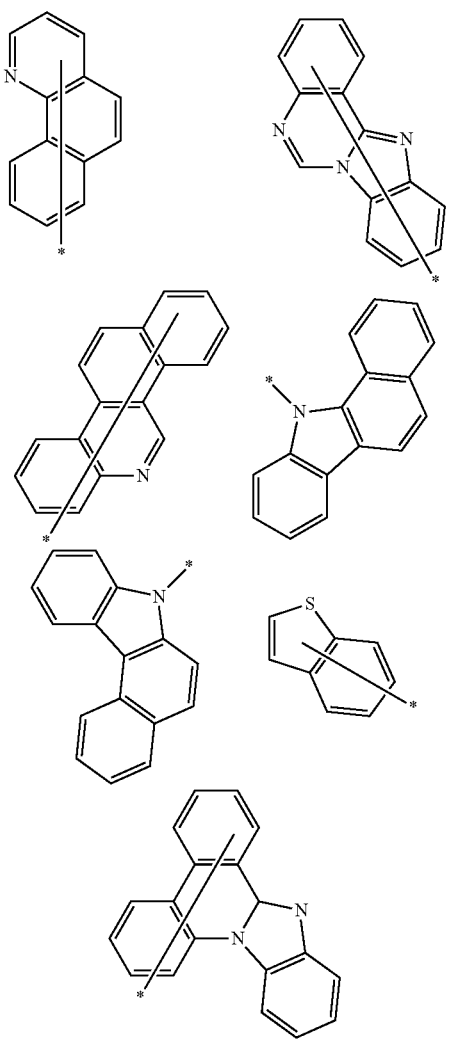

wherein the substituents in the table above are unsubstituted or additionally substituted with substituents selected from the group consisting of an alkyl group, an aryl group, and a heteroring group including one or more of N, O, S or P atoms; or when o≥ 2, a plurality of adjacent R4s together form a hydrocarbon ring substituted with at least one of the following substituents:

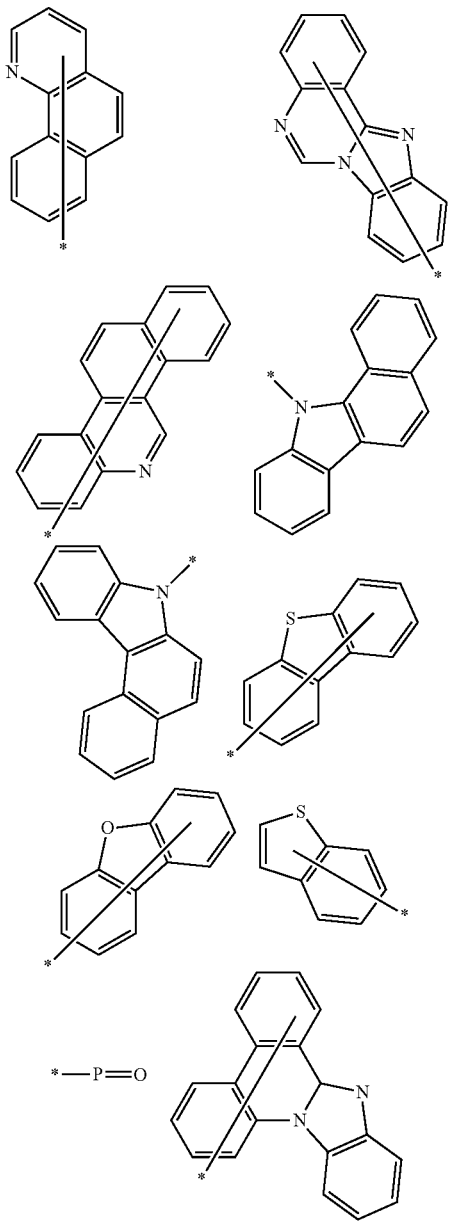

wherein the substituents in the table above are unsubstituted or additionally substituted with substituents selected from the group consisting of an alkyl group, an aryl group, and a heteroring group including one or more of N, O, S or P atoms;

when r≥ 2, R5s are the same as or different from each other; and

R5 is hydrogen, deuterium, a halogen group, a nitrile group, a nitro group, a hydroxy group, a substituted or unsubstituted alkyl group, a substituted or unsubstituted cycloalkyl group, a substituted or unsubstituted alkoxy group, a substituted or unsubstituted phosphine oxide group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, an unsubstituted amine group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, a substituted or unsubstituted fluorenyl group, an unsubstituted carbazole group, or an unsubstituted heteroring group including one or more of N, O, S and P atoms, or adjacent groups among a plurality of R5s are bonded to each other to form an aliphatic ring, an aromatic ring, an aliphatic heteroring or an aromatic heteroring, or form a spiro bond.

2. The fluoranthene compound of claim 1, wherein the compound of Chemical Formula 1 has the following Chemical Formula 2:

[Chemical Formula 2]

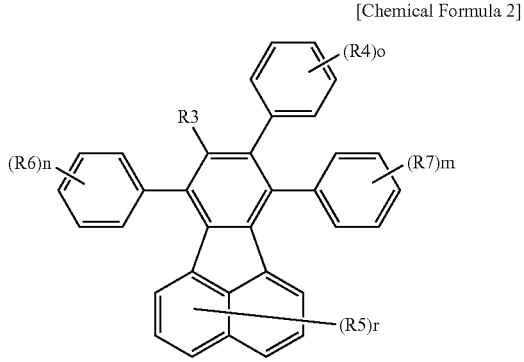

wherein, in Chemical Formula 2:
o, r, and R3 to R5 are the same as those defined in Chemical Formula 1;
each of n and m is an integer of 0 to 5;
when n≥ 2, R6s are the same as or different from each other;
when m≥ 2, R7s are the same as or different from each other; and
R6 ; and R7 are the same as or different from each other, each independently hydrogen, deuterium, a halogen group, a nitrile group, a nitro group, a hydroxy group, a substituted or unsubstituted alkyl group, a substituted or unsubstituted cycloalkyl group, a substituted or unsubstituted alkoxy group, a substituted or unsubstituted phosphine oxide group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, a substituted or unsubstituted fluorenyl group, a substituted or unsubstituted carbazole group, or a substituted or unsubstituted heterozing group including one or more of N, O, S and P atoms, or adjacent groups may be bonded to each other to form an aliphatic ring, an aromatic ring, an aliphatic heteroring or an aromatic heteroring, or form a spiro bond.

3. The fluoranthene compound of claim 1, wherein the substituents are additionally substituted with hydrogen, a methyl group, an ethyl group; a phenyl group, a naphthyl group, a biphenyl group, or a pyridine group.

4. The fluoranthene compound of claim 1, wherein Chemical Formula 1 is any one of the following Compounds:

Compound 1

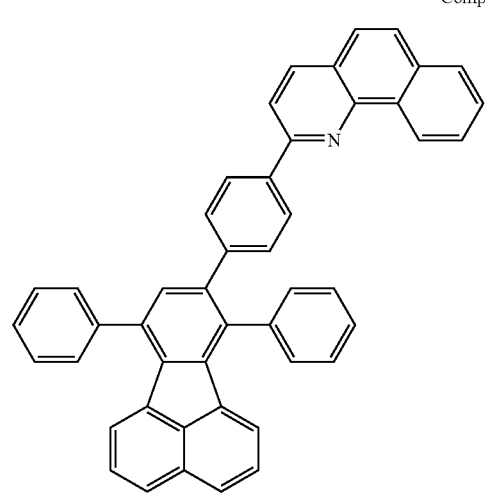

Compound 14

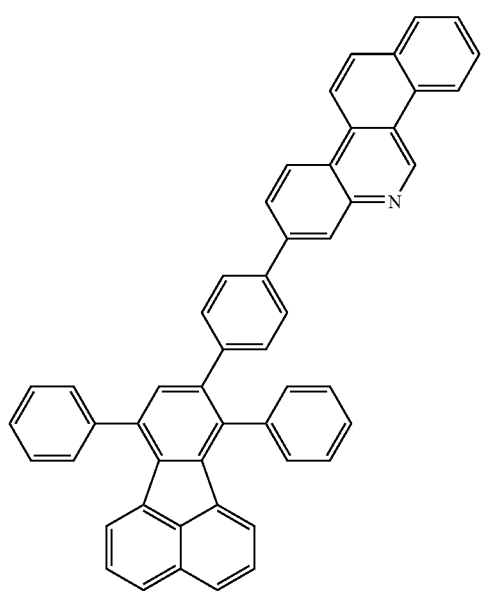

Compound 17

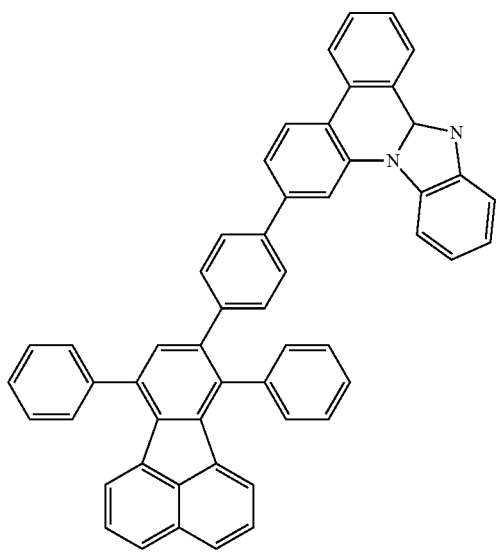

Compound 18

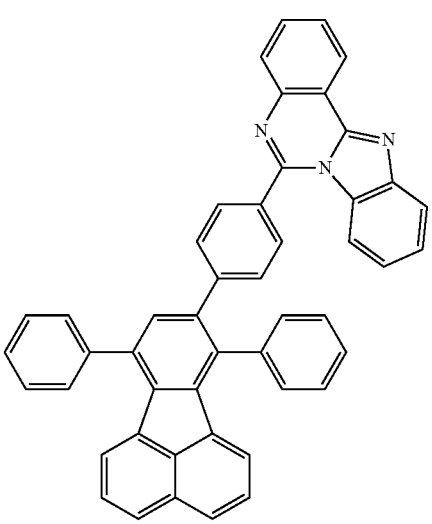

-continued
Compound 19
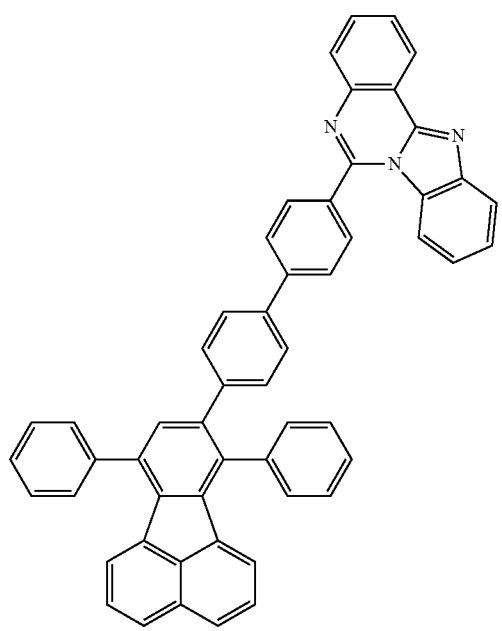
Compound 20
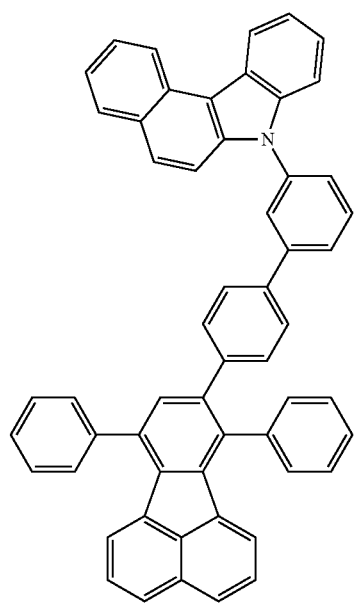
Compound 21
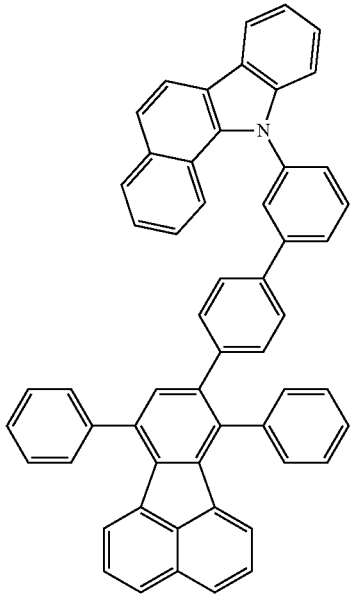
Compound 22
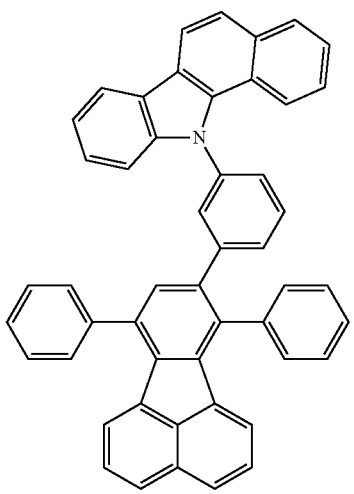
Compound 23
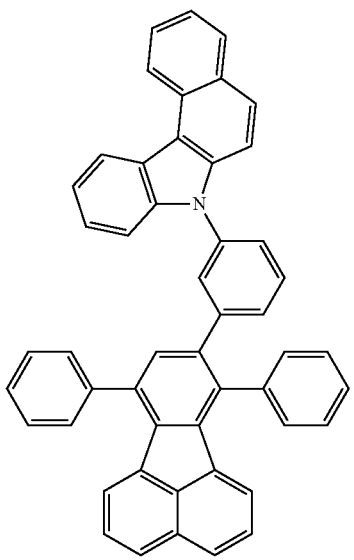

-continued
Compound 24
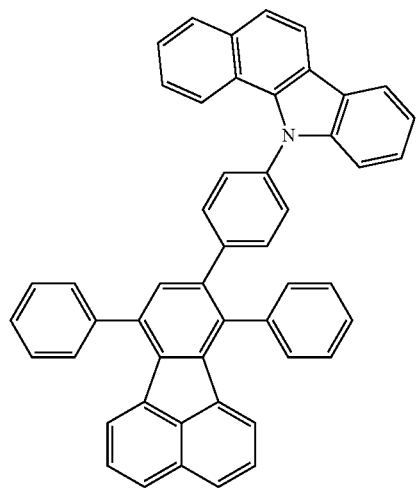
Compound 25
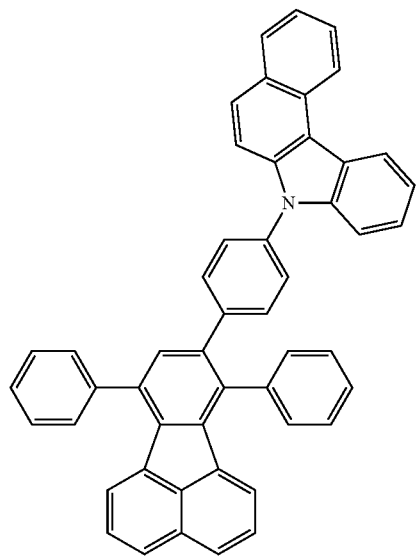
Compound 28
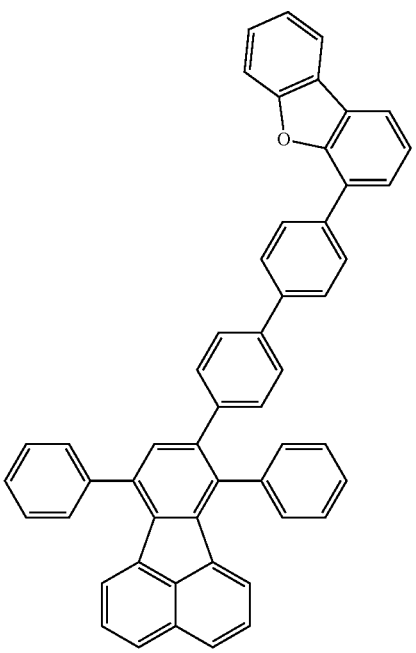
Compound 29
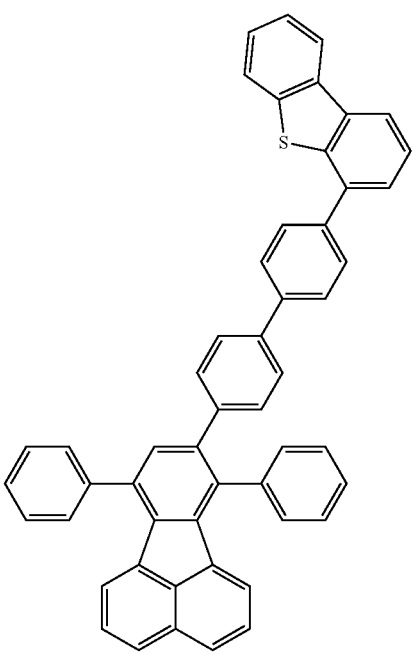

Compound 32

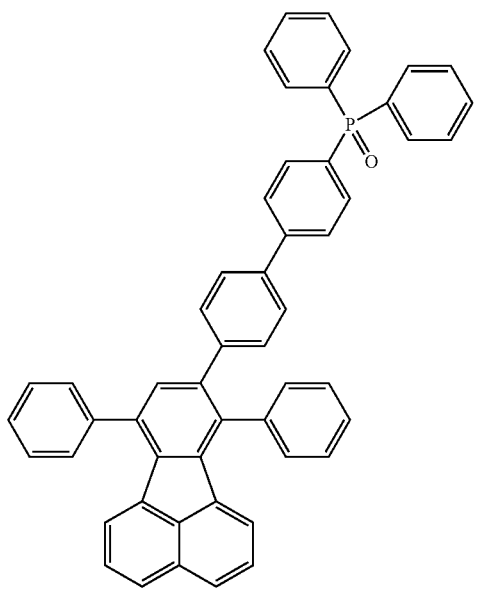

Compound 33

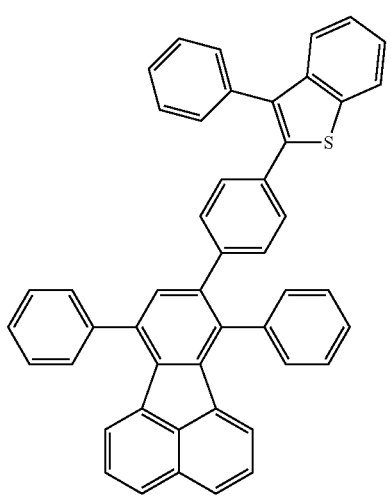

Compound 36

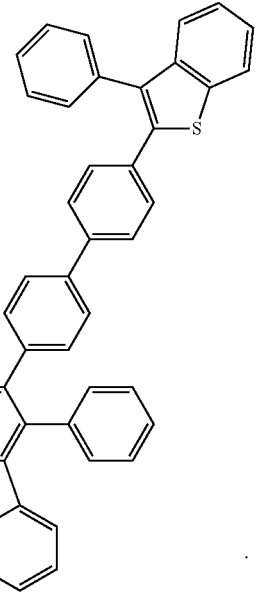

5. An organic electronic device comprising:
a first electrode;
a second electrode; and
one or more layers of organic material layers provided between the first electrode and the second electrode,
wherein one or more layers of the organic material layers include the fluoranthene compound of claim 1.

6. The organic electronic device of claim 5, which is selected from the group consisting of an organic light emitting device, an organic solar cell and an organic transistor.

7. The organic electronic device of claim 5, which is an organic light emitting device comprising:
a first electrode;
a second electrode; and
one or more layers of organic material layers including a light emitting layer provided between the first electrode and the second electrode,
wherein one or more layers of the organic material layers include the fluoranthene compound.

8. The organic electronic device of claim 7, wherein the organic material layer includes an electron transfer layer, an electron injection layer, or a layer that transfers and injects electrons at the same time, and the electron transfer layer, the electron injection layer, or the layer that transfers and injects electrons at the same time includes the fluoranthene compound.

9. The organic electronic device of claim 7, wherein the light emitting layer includes the fluoranthene compound.

10. The organic electronic device of claim 7, wherein the organic material layer includes a hole transfer layer or a hole injection layer, and the hole transfer layer or the hole injection layer includes the fluoranthene compound.

11. The organic electronic device of claim 7, wherein the organic material layer includes one, two or more layers selected from the group consisting of the hole injection layer, the hole transfer layer, the electron transfer layer, the electron injection layer, an electron blocking layer and a hole blocking layer.

12. An organic solar cell, comprising:

a first electrode;

a second electrode; and one or more layers of organic material layers including a photoactive layer provided between the first electrode and the second electrode, wherein one or more layers of the organic material layers include a fluoranthene compound of Chemical Formula 1:

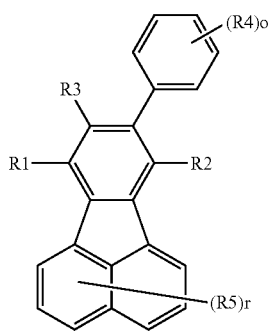

[Chemical Formula 1]

wherein, in Chemical Formula 1:

R1 to R3 are groups of the formula -(L)p-(Y)q;

p is an integer of 0 to 10 and q is an integer of 1 to 10;

o is an integer of 1 to 5;

r is an integer of 0 to 6;

L is a substituted or unsubstituted arylene group, a substituted or unsubstituted alkenylene group, a substituted or unsubstituted fluorenylene group, or a substituted or unsubstituted heteroarylene group having O, N, S or P as a heteroatom;

Y is hydrogen, deuterium, a halogen group, a nitrile group, a nitro group, a hydroxy group, a substituted or unsubstituted alkyl group, a substituted or unsubstituted cycloalkyl group, a substituted or unsubstituted alkoxy group, a substituted or unsubstituted phosphine oxide group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, a substituted or unsubstituted fluorenyl group, a substituted or unsubstituted carbazole group, or a substituted or unsubstituted heteroring group including one or more of N, O, S and P atoms;

when p≥2 or q≥2, Ls or Ys are the same as or different from each other;

R1 and R3 may be bonded to each other to form an aliphatic ring, an aromatic ring, an aliphatic heteroring or an aromatic heteroring, or form a spiro bond;

when o≥ 2; , R4s are the same as or different from each other;

R4 is a phenyl group substituted with at least one of the following substituents, or is at least one of the following substituents, or a plurality of adjacent R4s form a hydrocarbon ring substituted with at least one of the following substituents with each other:

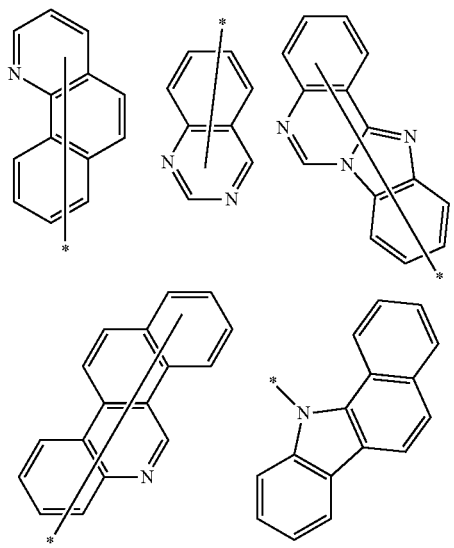

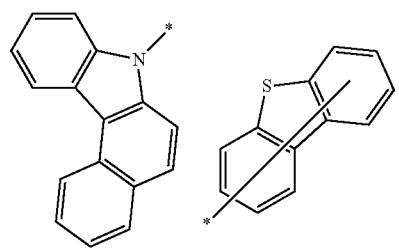

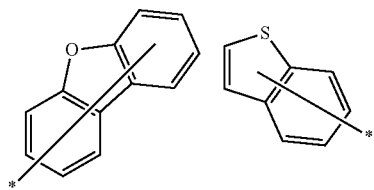

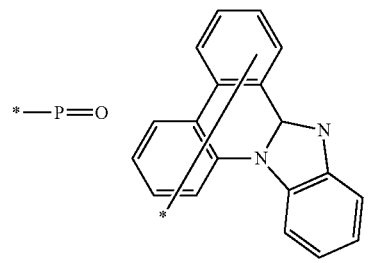

wherein the substituents in the table above are unsubstituted or additionally substituted with substituents selected from the group consisting of an alkyl group, an aryl group, and a heteroring group including one or more of N, O, S or P atoms;

when r≥ 2, R5s are the same as or different from each other; and

R5 is hydrogen, deuterium, a halogen group, a nitrile group, a nitro group, a hydroxy group, a substituted or unsubstituted alkyl group, a substituted or unsubstituted cycloalkyl group, a substituted or unsubstituted alkoxy group, a substituted or unsubstituted phosphine oxide group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, a substituted or unsubstituted fluorenyl group, a substituted or unsubstituted carbazole group, or a substituted or unsubstituted heteroring group including one or more of N, O, S and P atoms, or adjacent groups among a plurality of R5s are bonded to each other to form an aliphatic ring, an aromatic ring, an aliphatic heteroring or an aromatic heteroring, or form a spiro bond.

13. The organic solar cell of claim 12, wherein the organic material layer includes a photoactive layer, and the photoactive layer includes the fluoranthene compound.

14. The organic solar cell of claim 12, wherein the fluoranthene compound of Chemical Formula 1 is any one of the following compounds:

Compound 1

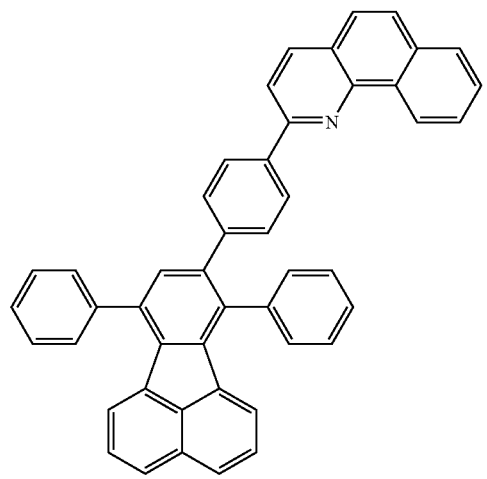

Compound 4

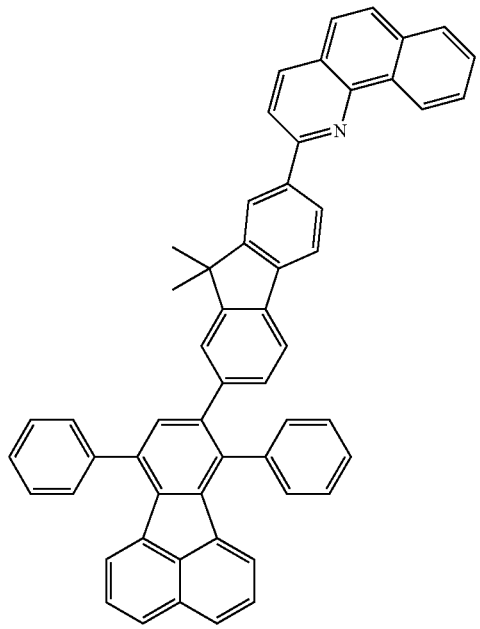

Compound 14

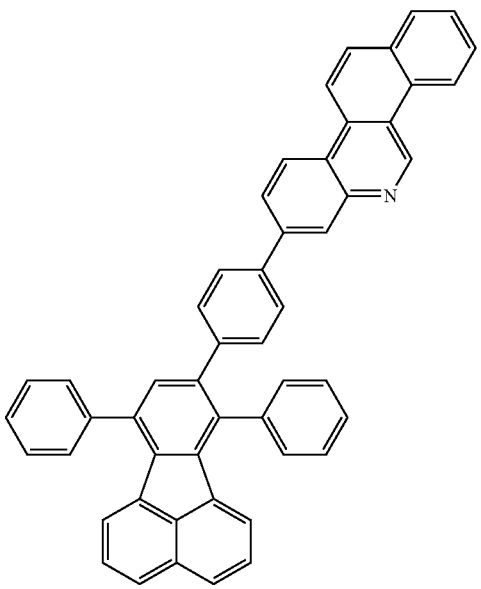

Compound 15
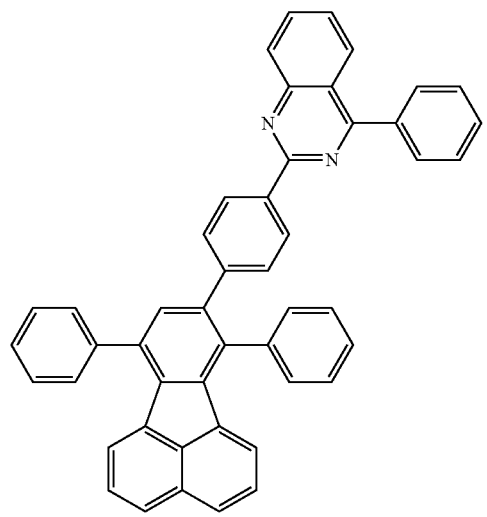
Compound 17
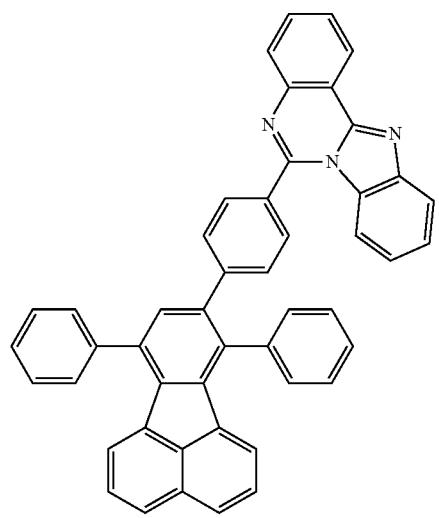
Compound 18
Compound 19
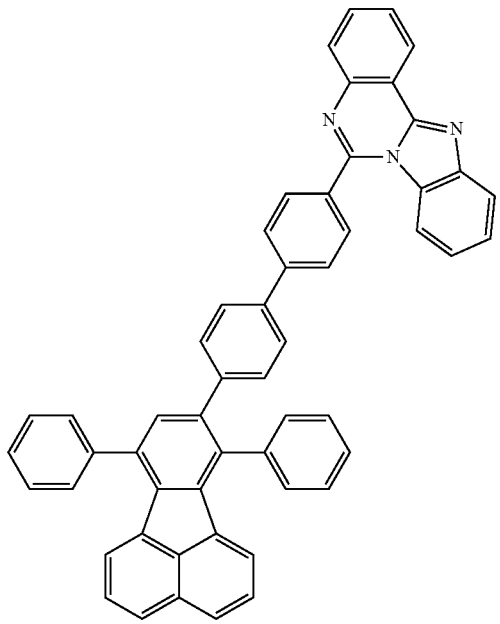
Compound 20
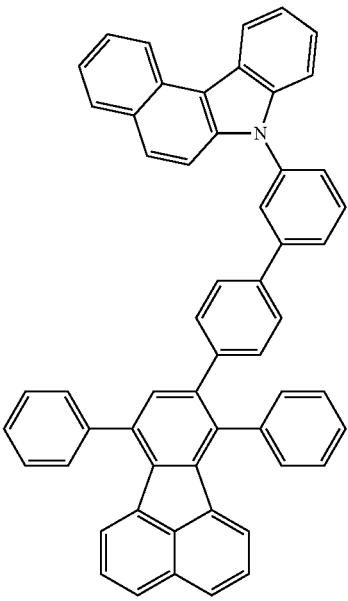

Compound 21
Compound 22
Compound 23
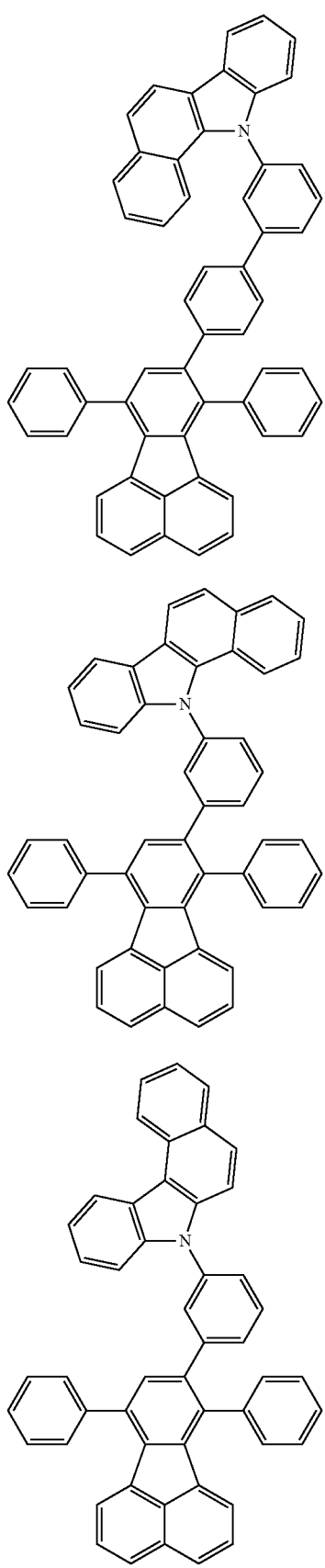
Compound 24
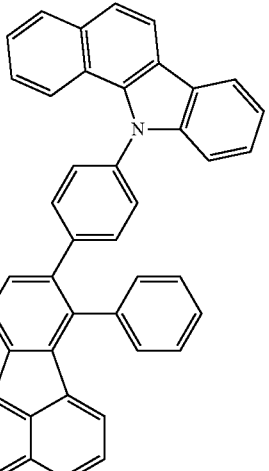
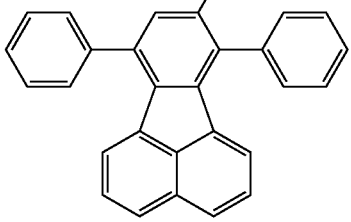
Compound 25
Compound 26
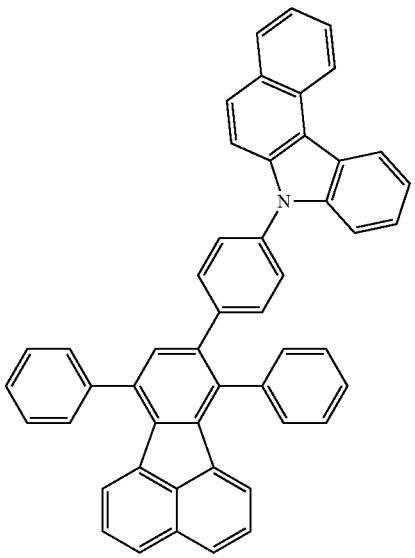

Compound 27
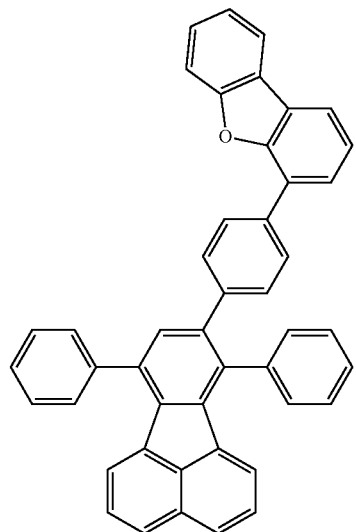
Compound 28
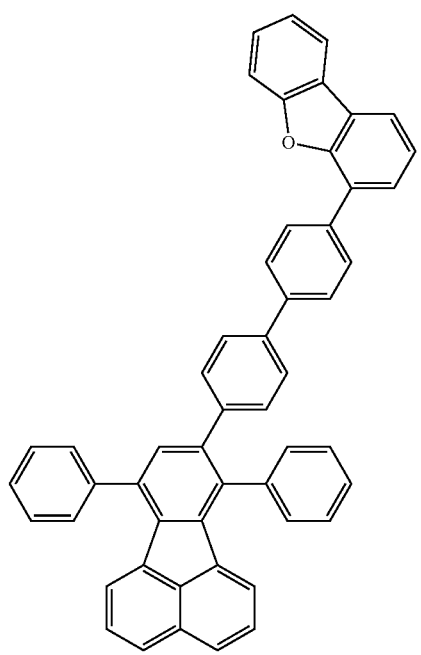
Compound 29
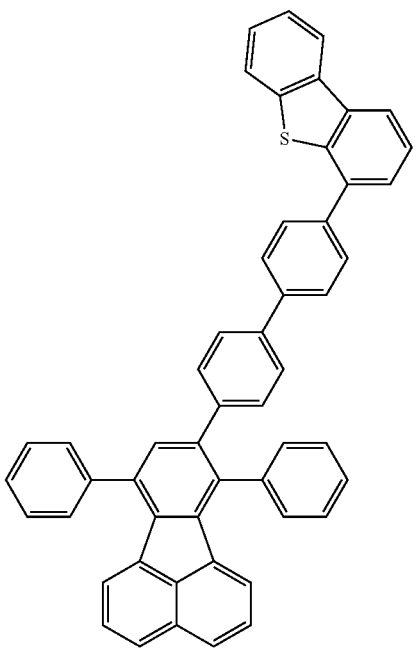
Compound 30
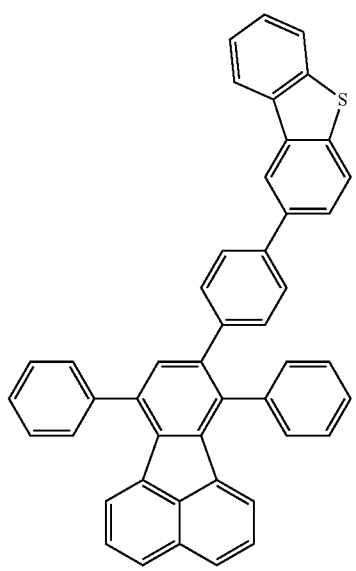

-continued

Compound 31

Compound 32

Compound 33

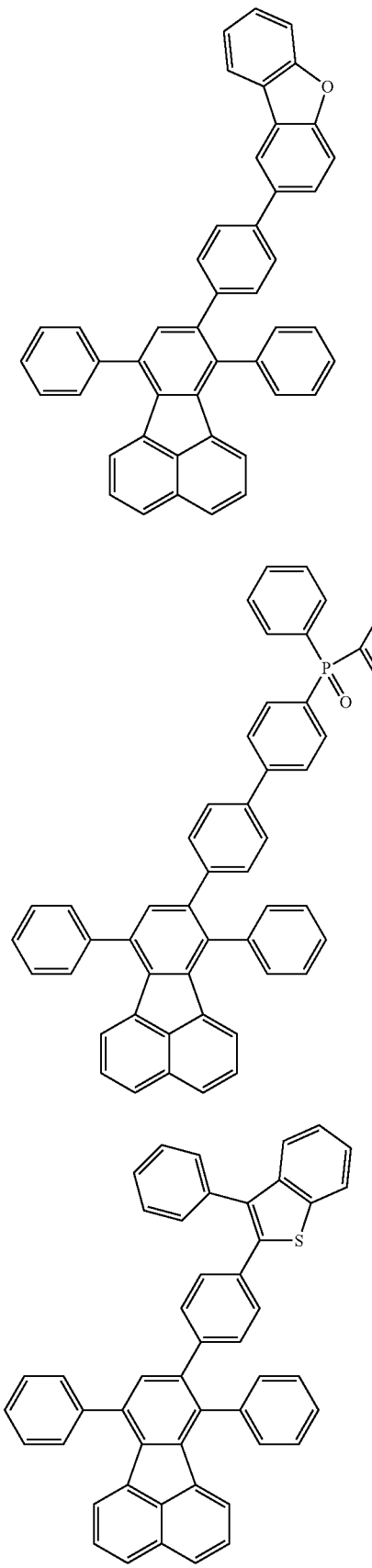

-continued

Compound 36

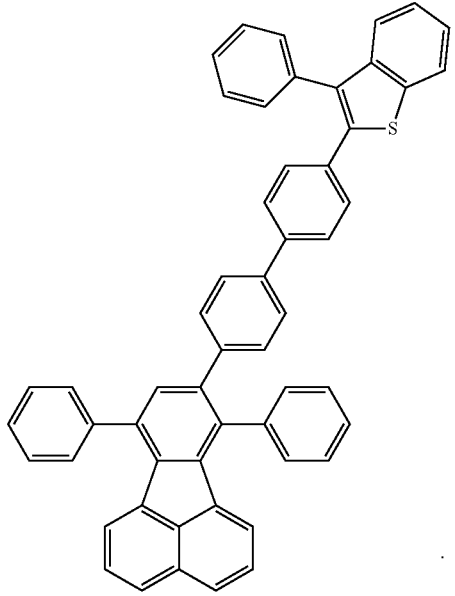

15. An organic transistor, comprising:
a source;
a drain;
a gate; and
one or more organic material layers, wherein one or more of the organic material layers include a fluoranthene compound of Chemical Formula 1:

[Chemical Formula 1]

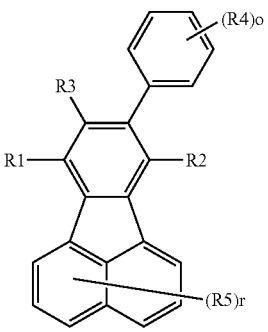

wherein, in Chemical Formula 1:
R1 to R3 are groups of the formula -(L)p-(Y)q;
p is an integer of 0 to 10 and q is an integer of 1 to 10;
o is an integer of 1 to 5;
r is an integer of 0 to 6;
L is a substituted or unsubstituted arylene group, a substituted or unsubstituted alkenylene group, a substituted or unsubstituted fluorenylene group, or a substituted or unsubstituted heteroarylene group having O, N, S or P as a heteroatom;
Y is hydrogen, deuterium, a halogen group, a nitrile group, a nitro group, a hydroxy group, a substituted or unsubstituted alkyl group, a substituted or unsubstituted cycloalkyl group, a substituted or unsubstituted alkoxy group, a substituted or unsubstituted phosphine oxide group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, a substituted or unsubstituted fluorenyl group, a substituted or unsubstituted carbazole group, or a substituted or unsubstituted heteroring group including one or more of N, O, S and P atoms;

when p≥2 or q≥2, Ls or Ys are the same as or different from each other;

R1 and R3 may be bonded to each other to form an aliphatic ring, an aromatic ring, an aliphatic heteroring or an aromatic heteroring, or form a spiro bond;

when o≥ 2, R4s are the same as or different from each other;

R4 is a phenyl group substituted with at least one of the following substituents, or is at least one of the following substituents, or a plurality of adjacent R4s form a hydrocarbon ring substituted with at least one of the following substituents with each other:

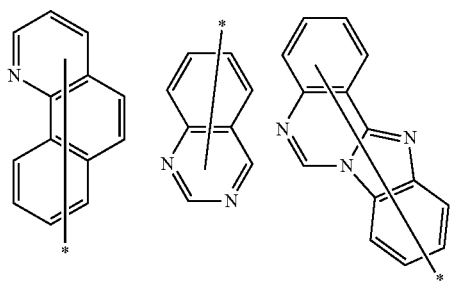

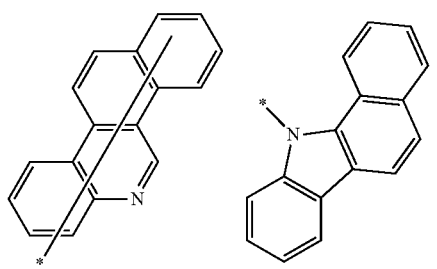

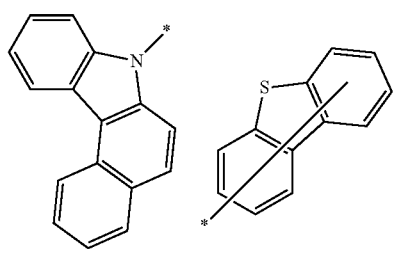

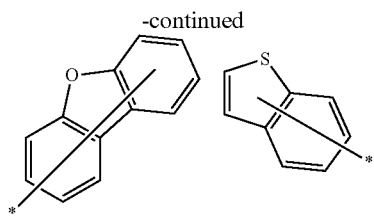

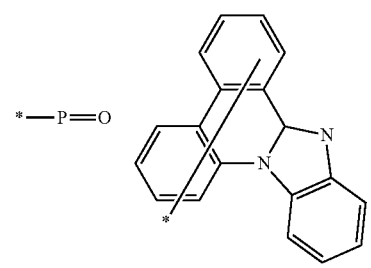

wherein the substituents in the table above are unsubstituted or additionally substituted with substituents selected from the group consisting of an alkyl group, an aryl group, and a heteroring group including one or more of N, O, S or P atoms;

when r≥ 2, R5s are the same as or different from each other; and

R5; is hydrogen, deuterium, a halogen group, a nitrile group, a nitro group, a hydroxy group, a substituted or unsubstituted alkyl group, a substituted or unsubstituted cycloalkyl group, a substituted or unsubstituted alkoxy group, a substituted or unsubstituted phosphine oxide group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, a substituted or unsubstituted fluorenyl group, a substituted or unsubstituted carbazole group, or a substituted or unsubstituted heteroring group including one or more of N, O, S and P atoms, or adjacent groups among a plurality of R5s are bonded to each other to form an aliphatic ring, an aromatic ring, an aliphatic heteroring or an aromatic heteroring, or form a spiro bond.

16. The organic transistor of claim 15, wherein the fluoranthene compound of Chemical Formula 1 is any one of the following compounds:

Compound 1
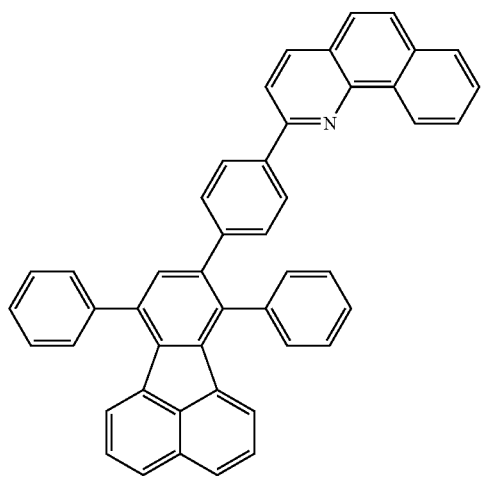
Compound 4
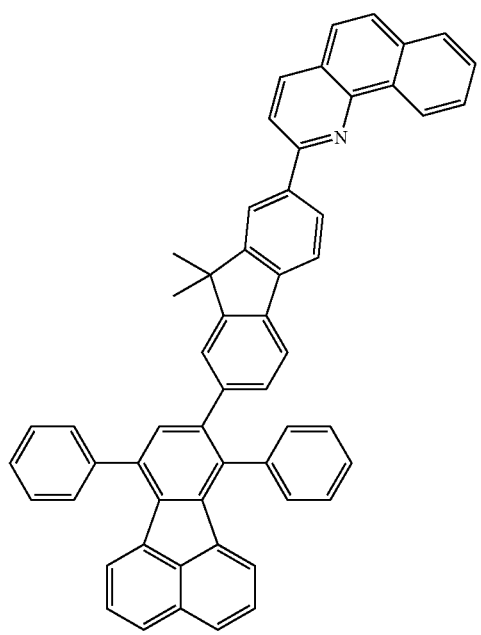
Compound 14
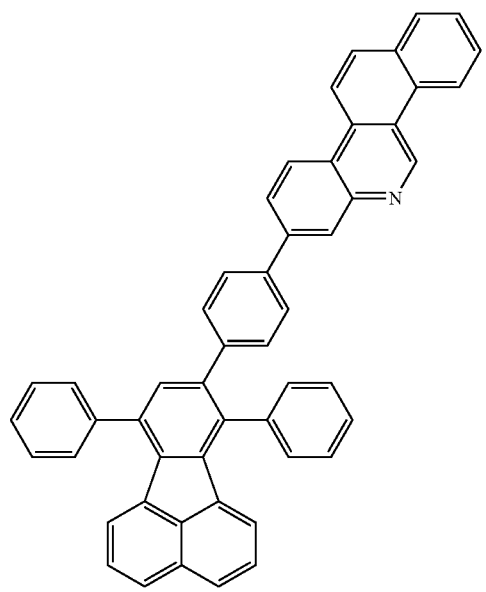
Compound 15
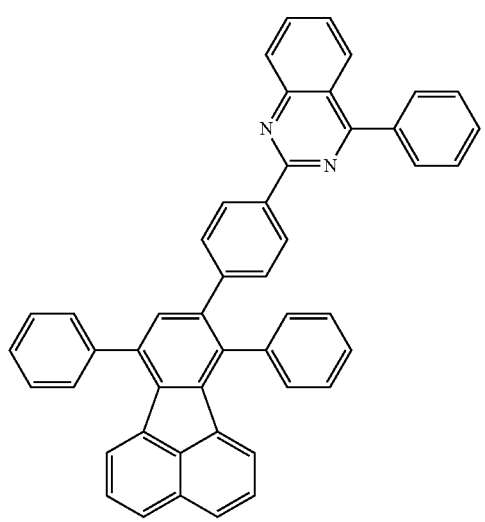

Compound 17
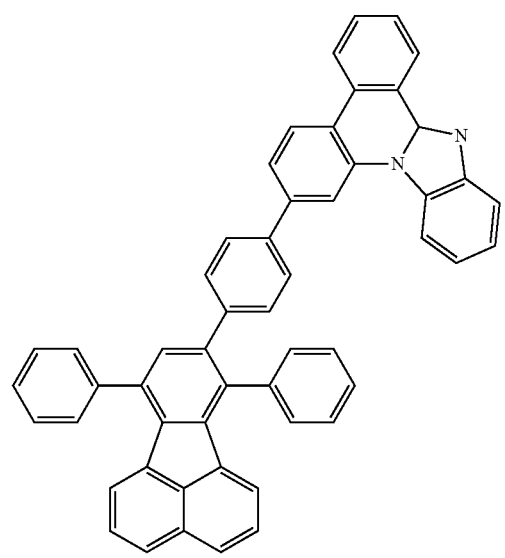
Compound 18
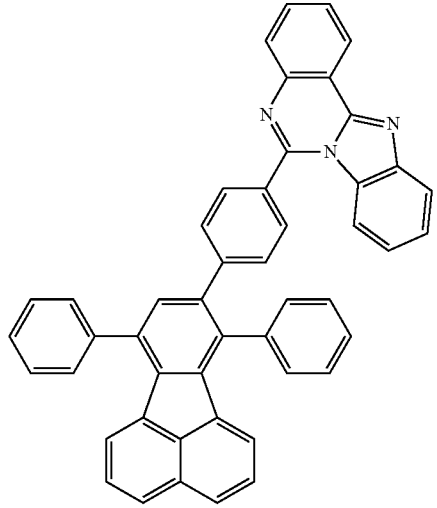
Compound 19
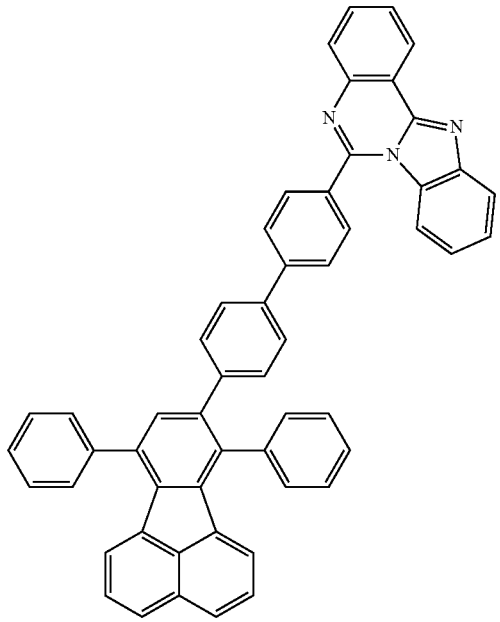
Compound 20
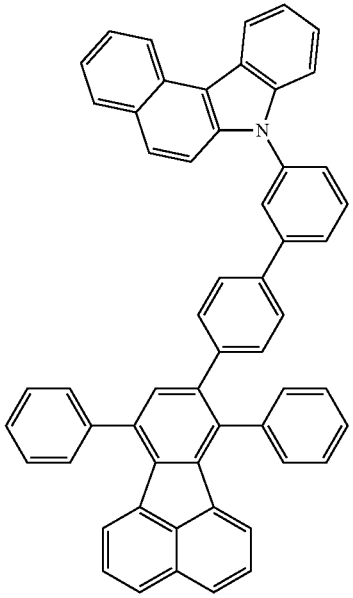

-continued
Compound 21
Compound 22
Compound 23
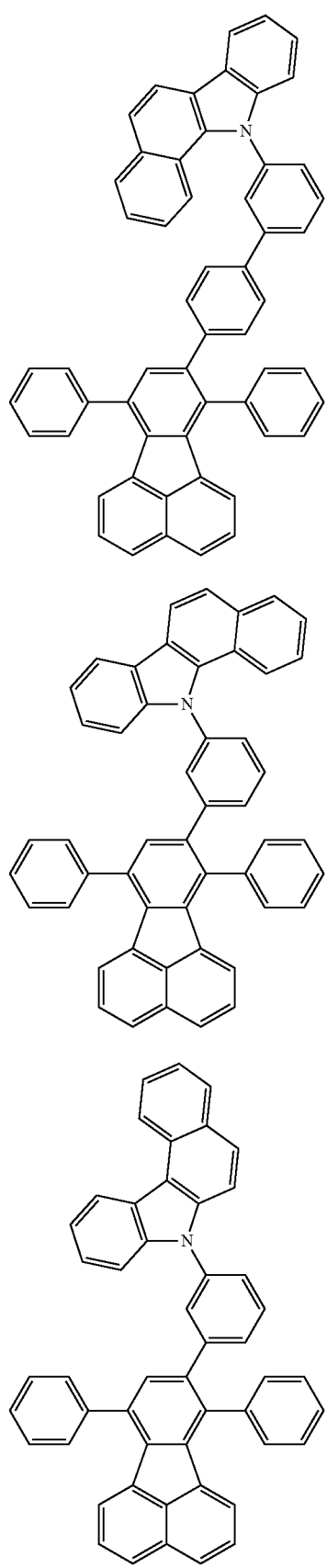
-continued
Compound 24
Compound 25
Compound 26
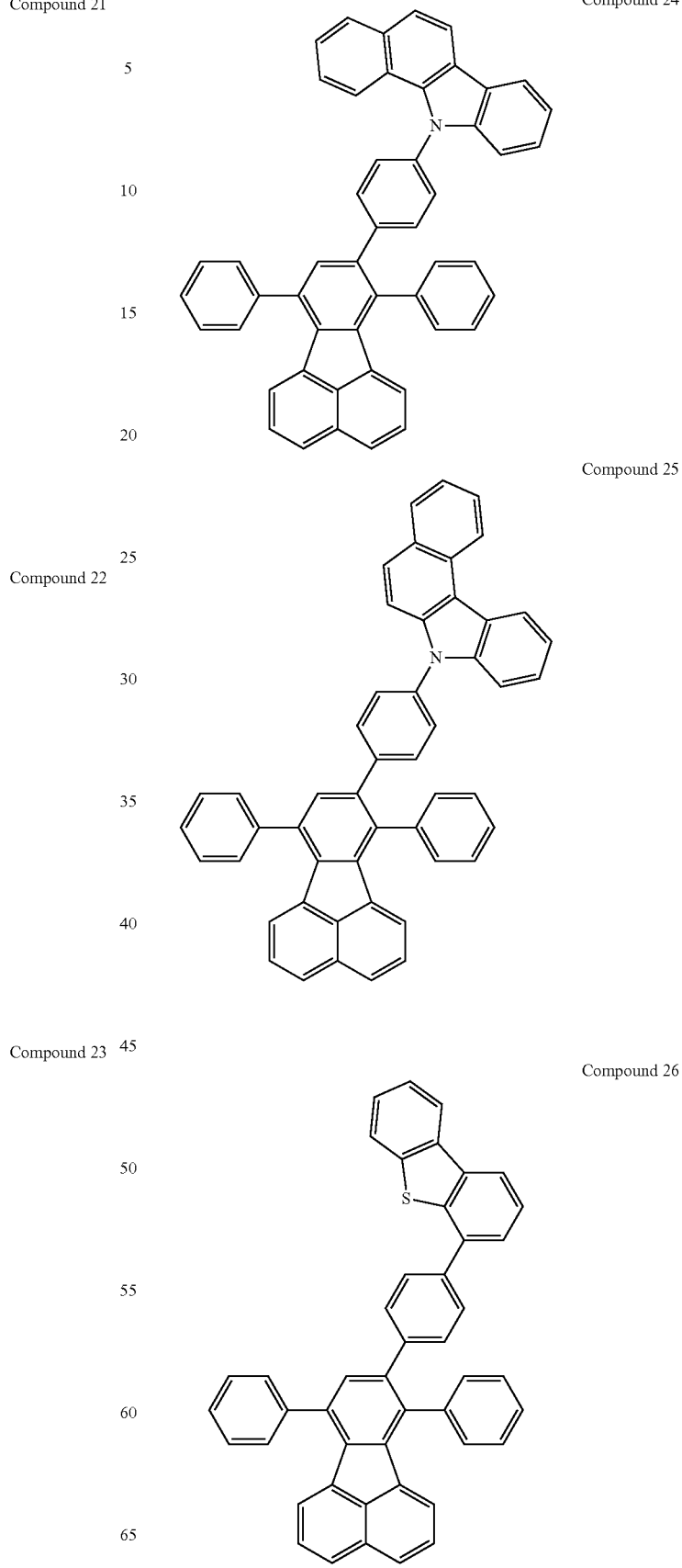

Compound 27
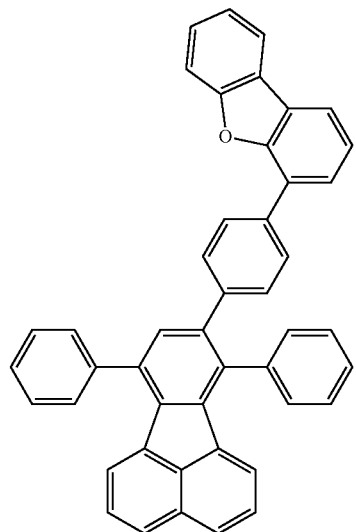
Compound 28
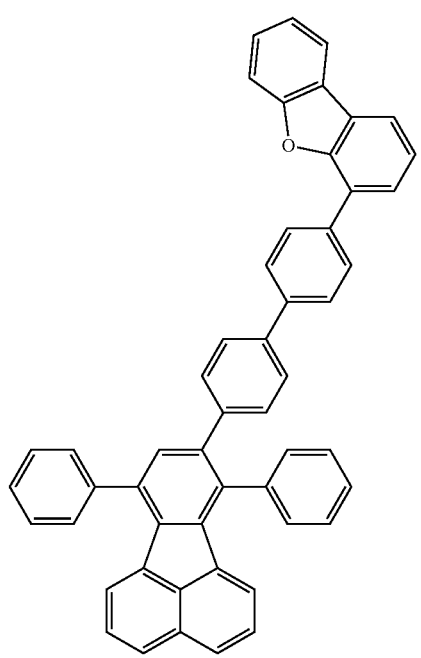
Compound 29
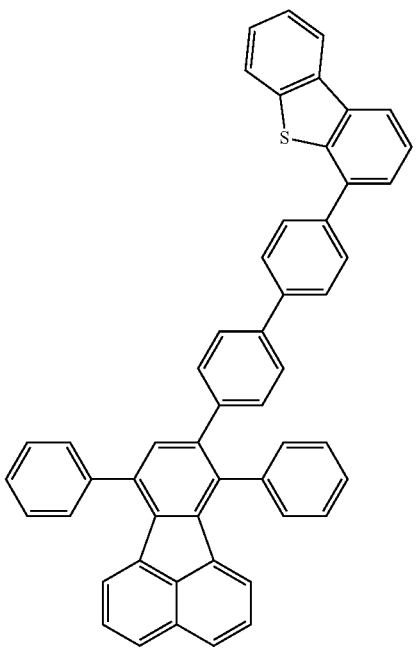
Compound 30
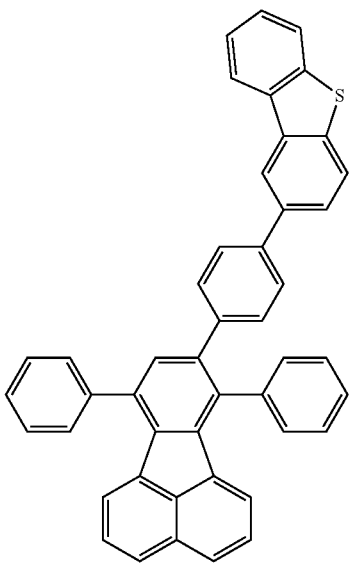

Compound 31
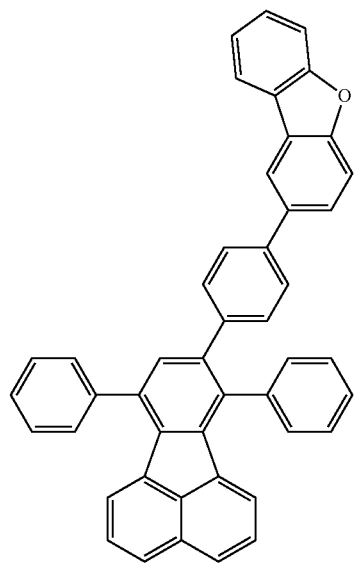
Compound 33
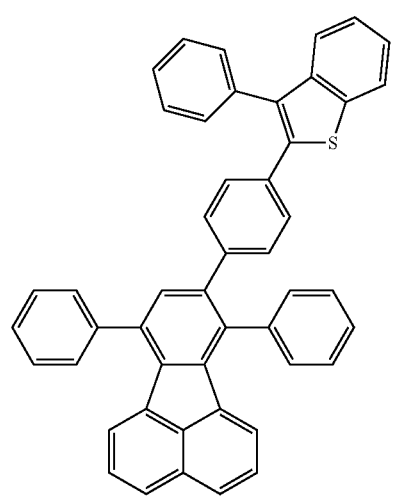
Compound 32
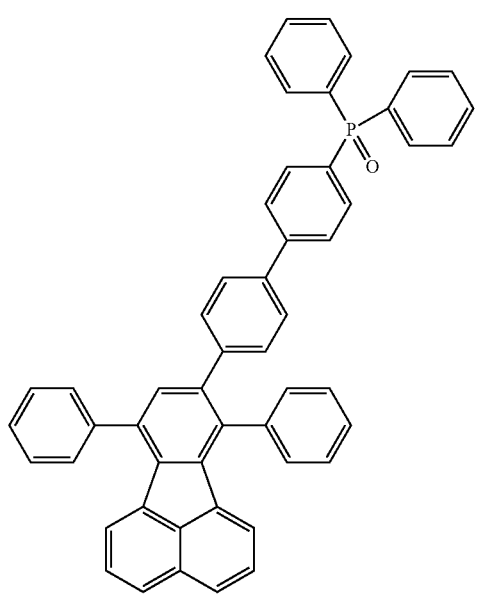
Compound 36
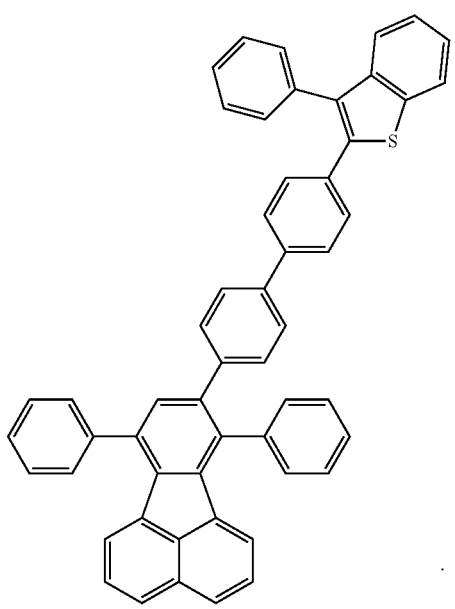
* * * * *

UNITED STATES PATENT AND TRADEMARK OFFICE
CERTIFICATE OF CORRECTION

PATENT NO. : 10,680,182 B2
APPLICATION NO. : 14/429258
DATED : June 9, 2020
INVENTOR(S) : Boonjae Jang et al.

It is certified that error appears in the above-identified patent and that said Letters Patent is hereby corrected as shown below:

In the Claims

At Column 62, Lines 19, to Column 63, Line 5, please replace Claim 2 with the following claim:
2. The fluoranthene compound of Claim 1, wherein the compound of Chemical Formula 1 has the following Chemical Formula 2:
[Chemical Formula 2]

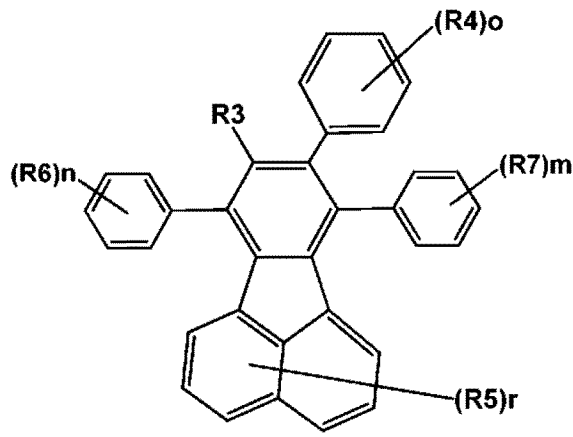

wherein, in Chemical Formula 2:
    o, r, and R3 to R5 are the same as those defined in Chemical Formula 1;
    each of n and m is an integer of 0 to 5;
    when $n \geq 2$, R6s are the same as or different from each other;
    when $m \geq 2$, R7s are the same as or different from each other; and
    R6 and R7 are the same as or different from each other, each independently hydrogen, deuterium, a halogen group, a nitrile group, a nitro group, a hydroxy group, a substituted or unsubstituted alkyl group, a substituted or unsubstituted cycloalkyl group, a substituted or unsubstituted alkoxy group, a substituted or unsubstituted phosphine oxide group, a substituted or unsubstituted aryloxy group, a substituted or unsubstituted alkylthioxy group, a substituted or unsubstituted arylthioxy group, a Signed and Sealed this
Eighth Day of September, 2020

Andrei Iancu
*Director of the United States Patent and Trademark Office* substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, a substituted or unsubstituted fluorenyl group, a substituted or unsubstituted carbazole group, or a substituted or unsubstituted heteroring group including one or more of N, O, S and P atoms, or adjacent groups may be bonded to each other to form an aliphatic ring, an aromatic ring, an aliphatic heteroring or an aromatic heteroring, or form a spiro bond.